US012806026B2

(12) United States Patent
Harris, Jr.

(10) Patent No.: US 12,806,026 B2
(45) Date of Patent: Nov. 24, 2026

(54) TIBIAL COMPONENT OF ENDOPROSTHETIC KNEE IMPLANT, KITS AND INSTRUMENTS THEREFORE, AND METHODS OF USE

(71) Applicant: MicroPort Orthopedics Holdings Inc., Arlington, TN (US)

(72) Inventor: Brian R. Harris, Jr., Cordova, TN (US)

( * ) Notice: Subject to any disclaimer, the term of this patent is extended or adjusted under 35 U.S.C. 154(b) by 1008 days.

(21) Appl. No.: 18/053,196

(22) Filed: Nov. 7, 2022

(65) Prior Publication Data

US 2023/0157831 A1 May 25, 2023

Related U.S. Application Data

(60) Provisional application No. 63/264,332, filed on Nov. 19, 2021.

(51) Int. Cl.
*A61F 2/38* (2006.01)
*A61F 2/30* (2006.01)

(52) U.S. Cl.
CPC .... *A61F 2/389* (2013.01); *A61F 2002/30616* (2013.01); *A61F 2002/30884* (2013.01)

(58) Field of Classification Search
CPC .................. A61F 2/389; A61F 2/30749; A61F 2002/30884
See application file for complete search history.

(56) References Cited

U.S. PATENT DOCUMENTS

| | | | |
|---|---|---|---|
| 2,246,066 | A | 6/1941 | Frank |
| 4,081,866 | A | 4/1978 | Upshaw et al. |
| 4,340,978 | A | 7/1982 | Buechel et al. |
| 4,662,889 | A | 5/1987 | Zichner et al. |
| 4,769,040 | A | 9/1988 | Wevers |
| 4,888,020 | A | 12/1989 | Horber |
| 4,944,756 | A | 7/1990 | Kenna |
| 4,950,298 | A | 8/1990 | Gustilo et al. |
| 4,959,071 | A | 9/1990 | Brown et al. |
| 5,007,933 | A | 4/1991 | Sidebotham et al. |

(Continued)

FOREIGN PATENT DOCUMENTS

| | | |
|---|---|---|
| CA | 2839431 | 12/2012 |
| CN | 102006839 A | 4/2011 |

(Continued)

OTHER PUBLICATIONS

Storer, John, Written Opinion of the International Searching Authority for Int'l App. No. PCT/US2022/079430, Mar. 30, 2023, European Patent Office, Rijswijk, Netherlands.

(Continued)

*Primary Examiner* — Javier G Blanco

(57) ABSTRACT

The present disclosure relates to a tibial component for an endoprosthetic knee implant comprising a tibial baseplate and a keel extending from a lower surface of the tibial baseplate. The tibial baseplate is disposed at a keel posterior angle relative to the keel, and the tibial baseplate is also disposed at a keel varus angle relative to the keel. The disclosure further describes modular keel embodiments, exemplary instruments that can be used to implant exemplary tibial components into and onto the proximal tibia, methods related thereto, and kits therefore.

20 Claims, 17 Drawing Sheets

(56) References Cited

U.S. PATENT DOCUMENTS

| | | | |
|---|---|---|---|
| 5,035,700 | A | 7/1991 | Kenna |
| 5,061,271 | A | 10/1991 | Van Zile |
| 5,084,982 | A | 2/1992 | Feng |
| 5,133,758 | A | 7/1992 | Hollister |
| 5,133,760 | A | 7/1992 | Petersen et al. |
| 5,137,536 | A | 8/1992 | Koshino |
| 5,226,915 | A | 7/1993 | Bertin |
| 5,282,861 | A | 2/1994 | Kaplan |
| 5,282,869 | A | 2/1994 | Miyajima et al. |
| 5,326,361 | A | 7/1994 | Hollister |
| 5,330,532 | A | 7/1994 | Ranawat |
| 5,445,642 | A | 8/1995 | McNulty et al. |
| 5,519,942 | A | 5/1996 | Webb |
| 5,549,686 | A | 8/1996 | Johnson et al. |
| 5,549,688 | A | 8/1996 | Ries et al. |
| 5,609,643 | A | 3/1997 | Colleran et al. |
| 5,681,354 | A | 10/1997 | Eckhoff |
| 5,688,279 | A | 11/1997 | McNulty et al. |
| 5,702,460 | A | 12/1997 | Carls et al. |
| 5,722,179 | A | 3/1998 | Zanier |
| 5,728,162 | A | 3/1998 | Eckhoff |
| 5,776,201 | A | 7/1998 | Colleran et al. |
| 5,824,105 | A | 10/1998 | Ries et al. |
| 5,871,546 | A | 2/1999 | Colleran et al. |
| 5,879,354 | A | 3/1999 | Haines et al. |
| 5,879,393 | A | 3/1999 | Whiteside et al. |
| 5,935,173 | A | 8/1999 | Roger et al. |
| 6,013,103 | A | 1/2000 | Kaufman et al. |
| 6,039,764 | A | 3/2000 | Pottenger et al. |
| 6,074,424 | A | 6/2000 | Perrone, Jr. et al. |
| 6,096,082 | A | 8/2000 | Stegmuller et al. |
| 6,106,529 | A | 8/2000 | Techiera |
| 6,152,960 | A | 11/2000 | Pappas |
| 6,197,064 | B1 | 3/2001 | Haines et al. |
| 6,217,619 | B1 | 4/2001 | Keller |
| 6,235,060 | B1 | 5/2001 | Kubein-Meesenburg et al. |
| 6,264,697 | B1 | 7/2001 | Walker |
| 6,325,828 | B1 | 12/2001 | Dennis et al. |
| 6,364,911 | B1 | 4/2002 | Schmotzer et al. |
| 6,421,927 | B1 | 7/2002 | Bach et al. |
| 6,540,786 | B2 | 4/2003 | Chibrac et al. |
| 6,540,787 | B2 | 4/2003 | Biegun et al. |
| 6,589,283 | B1 | 7/2003 | Metzger et al. |
| 6,616,696 | B1 | 9/2003 | Merchant |
| 6,699,291 | B1 | 3/2004 | Augoyard et al. |
| 6,712,856 | B1 | 3/2004 | Carignan et al. |
| 6,743,258 | B1 | 6/2004 | Keller |
| 6,770,099 | B2 | 8/2004 | Andriacchi et al. |
| 6,802,865 | B2 | 10/2004 | Biegun et al. |
| 6,846,329 | B2 | 1/2005 | Mcminn |
| 6,893,467 | B1 | 5/2005 | Bercovy |
| 7,081,137 | B1 | 7/2006 | Servidio |
| 7,297,164 | B2 | 11/2007 | Johnson et al. |
| 7,306,609 | B2 | 12/2007 | Schmotzer et al. |
| 7,364,590 | B2 | 4/2008 | Siebel |
| 7,413,577 | B1 | 8/2008 | Servidio |
| 7,442,196 | B2 | 10/2008 | Fisher et al. |
| 7,465,320 | B1 | 12/2008 | Kito et al. |
| 7,678,152 | B2 | 3/2010 | Suguro et al. |
| 7,691,150 | B2 | 4/2010 | Cronin et al. |
| 7,695,520 | B2 | 4/2010 | Metzger et al. |
| 7,806,897 | B1 | 10/2010 | Bonutti |
| 7,981,159 | B2 | 7/2011 | Williams et al. |
| 8,062,377 | B2 | 11/2011 | Haines |
| 8,075,626 | B2 | 12/2011 | Dun |
| 8,088,167 | B2 | 1/2012 | Haines |
| 8,202,323 | B2 | 6/2012 | Wyss |
| 8,211,181 | B2 | 7/2012 | Walker |
| 8,292,964 | B2 | 10/2012 | Walker |
| 8,298,288 | B2 | 10/2012 | Walker |
| 8,357,202 | B2 | 1/2013 | Heggendom et al. |
| 8,377,141 | B2 | 2/2013 | Mcminn |
| 8,394,147 | B2 | 3/2013 | Otto et al. |
| 8,409,293 | B1 | 4/2013 | Howard et al. |
| 8,480,753 | B2 | 7/2013 | Collazo et al. |
| 8,480,754 | B2 | 7/2013 | Bojarski et al. |
| 8,500,816 | B2 | 8/2013 | Dees, Jr. et al. |
| 8,551,179 | B2 | 10/2013 | Jones et al. |
| 8,603,101 | B2 | 12/2013 | Claypool et al. |
| 8,721,732 | B2 | 5/2014 | Samuelson et al. |
| 8,771,365 | B2 | 7/2014 | Bojarski et al. |
| 8,911,502 | B2 | 12/2014 | Li et al. |
| 8,932,365 | B2 | 1/2015 | Parisi et al. |
| 9,003,672 | B2 | 4/2015 | Lozano, IV |
| 9,060,868 | B2 | 6/2015 | Parisi et al. |
| 9,173,744 | B2 | 11/2015 | Donno et al. |
| 9,308,095 | B2 | 4/2016 | Parisi et al. |
| 9,452,053 | B2 | 9/2016 | Wagner |
| 9,539,099 | B2 | 1/2017 | Heldreth et al. |
| 9,592,127 | B2 | 3/2017 | Earl et al. |
| 9,629,723 | B2 | 4/2017 | Parisi et al. |
| 9,788,955 | B2 | 10/2017 | Shah et al. |
| 9,839,521 | B2 | 12/2017 | Todd et al. |
| 9,867,708 | B2 | 1/2018 | Donna et al. |
| 9,956,048 | B2 | 5/2018 | Bojarski et al. |
| 9,962,264 | B2 | 5/2018 | Komistek |
| 9,993,345 | B2 | 6/2018 | Jones et al. |
| 10,045,850 | B2 | 8/2018 | Parisi et al. |
| 10,130,375 | B2 | 11/2018 | Yager et al. |
| 10,136,997 | B2 | 11/2018 | Yager |
| 10,322,004 | B2 | 6/2019 | Donno et al. |
| 10,433,966 | B2 | 10/2019 | Earl et al. |
| 10,568,742 | B2 | 2/2020 | Uthgenannt et al. |
| 10,582,982 | B2 | 3/2020 | Fisher et al. |
| 10,631,991 | B2 | 4/2020 | Yager |
| 10,939,923 | B2 | 3/2021 | Yager et al. |
| 2003/0153924 | A1 | 8/2003 | Kana et al. |
| 2003/0158606 | A1 | 8/2003 | Coon et al. |
| 2003/0225458 | A1 | 12/2003 | Donkers et al. |
| 2004/0039450 | A1 | 2/2004 | Griner et al. |
| 2004/0172137 | A1 | 9/2004 | Blaylock et al. |
| 2004/0204766 | A1* | 10/2004 | Siebel ..................... A61F 2/38 623/20.31 |
| 2004/0243245 | A1 | 12/2004 | Plumet et al. |
| 2004/0249467 | A1 | 12/2004 | Meyers et al. |
| 2005/0055102 | A1 | 3/2005 | Tomier et al. |
| 2005/0102032 | A1 | 5/2005 | Beynnon et al. |
| 2005/0107884 | A1 | 5/2005 | Johnson et al. |
| 2005/0143832 | A1 | 6/2005 | Carson |
| 2005/0177169 | A1 | 8/2005 | Fisher et al. |
| 2005/0283249 | A1 | 12/2005 | Carson |
| 2005/0283250 | A1 | 12/2005 | Coon et al. |
| 2005/0283251 | A1 | 12/2005 | Coon et al. |
| 2005/0283252 | A1 | 12/2005 | Coon et al. |
| 2005/0283253 | A1 | 12/2005 | Coon et al. |
| 2006/0028773 | A1 | 2/2006 | Shimazawa et al. |
| 2006/0129246 | A1 | 6/2006 | Steffensmeier |
| 2006/0142774 | A1 | 6/2006 | Metzger |
| 2006/0200163 | A1 | 9/2006 | Roger et al. |
| 2006/0224244 | A1 | 10/2006 | Thomas et al. |
| 2006/0235541 | A1 | 10/2006 | Hodorek |
| 2006/0235542 | A1 | 10/2006 | Hodorek et al. |
| 2006/0241634 | A1 | 10/2006 | Tuttle et al. |
| 2006/0265078 | A1 | 11/2006 | Mcminn |
| 2006/0265080 | A1 | 11/2006 | Mcminn |
| 2006/0287733 | A1 | 12/2006 | Bonuiti |
| 2007/0088444 | A1 | 4/2007 | Hodorek et al. |
| 2007/0123984 | A1 | 5/2007 | Hodorek |
| 2007/0135925 | A1 | 6/2007 | Walker |
| 2007/0135926 | A1 | 6/2007 | Walker |
| 2007/0150066 | A1 | 6/2007 | McMinn et al. |
| 2007/0179607 | A1 | 8/2007 | Hodorek et al. |
| 2007/0233269 | A1 | 10/2007 | Steines et al. |
| 2007/0260323 | A1 | 11/2007 | Earl et al. |
| 2008/0058947 | A1 | 3/2008 | Earl et al. |
| 2008/0058948 | A1 | 3/2008 | Biegun et al. |
| 2008/0097615 | A1 | 4/2008 | Lipman et al. |
| 2008/0097616 | A1 | 4/2008 | Meyers et al. |
| 2008/0114463 | A1 | 5/2008 | Auger et al. |
| 2008/0119940 | A1 | 5/2008 | Otto et al. |
| 2008/0140212 | A1 | 6/2008 | Metzger et al. |
| 2008/0184582 | A1 | 8/2008 | Kirn |
| 2008/0188855 | A1 | 8/2008 | Brown et al. |
| 2008/0188937 | A1 | 8/2008 | Ribic |

(56) References Cited

U.S. PATENT DOCUMENTS

| | | | |
|---|---|---|---|
| 2008/0188942 A1 | 8/2008 | Brown et al. | |
| 2008/0243258 A1 | 10/2008 | Sancheti | |
| 2008/0281428 A1 | 11/2008 | Meyers et al. | |
| 2008/0288080 A1 | 11/2008 | Sancheii | |
| 2009/0036992 A1 | 2/2009 | Tsakonas | |
| 2009/0043395 A1 | 2/2009 | Hotokebuchi et al. | |
| 2009/0062924 A1 | 3/2009 | Kito et al. | |
| 2009/0105772 A1 | 4/2009 | Seebeck et al. | |
| 2009/0132055 A1 | 5/2009 | Ferro | |
| 2009/0149963 A1 | 6/2009 | Sekel | |
| 2009/0222103 A1 | 9/2009 | Fitz et al. | |
| 2009/0265011 A1 | 10/2009 | Mandell | |
| 2009/0265013 A1 | 10/2009 | Mandell | |
| 2009/0306786 A1 | 12/2009 | Samuelson | |
| 2009/0306787 A1 | 12/2009 | Crabtree et al. | |
| 2009/0319047 A1 | 12/2009 | Walker | |
| 2009/0319048 A1 | 12/2009 | Shah et al. | |
| 2009/0319049 A1 | 12/2009 | Shah et al. | |
| 2009/0326663 A1 | 12/2009 | Dun | |
| 2009/0326665 A1 | 12/2009 | Wyss et al. | |
| 2009/0326666 A1 | 12/2009 | Wyss et al. | |
| 2009/0326667 A1 | 12/2009 | Williams et al. | |
| 2010/0036499 A1 | 2/2010 | Pinskerova | |
| 2010/0036500 A1 | 2/2010 | Heldreth et al. | |
| 2010/0042224 A1 | 2/2010 | Otto et al. | |
| 2010/0161067 A1 | 6/2010 | Saleh et al. | |
| 2010/0191298 A1 | 7/2010 | Earl et al. | |
| 2010/0211179 A1 | 8/2010 | Angibaud et al. | |
| 2010/0249657 A1 | 9/2010 | Nycz et al. | |
| 2010/0293802 A1 | 11/2010 | Stockman | |
| 2010/0305708 A1 | 12/2010 | Lang | |
| 2010/0329530 A1 | 12/2010 | Lang | |
| 2011/0022179 A1 | 1/2011 | Andriacchi et al. | |
| 2011/0029091 A1 | 2/2011 | Bojarski et al. | |
| 2011/0093083 A1 | 4/2011 | Earl et al. | |
| 2011/0099829 A1 | 5/2011 | Prior et al. | |
| 2011/0144760 A1 | 6/2011 | Wong et al. | |
| 2011/0190898 A1* | 8/2011 | Lenz | A61F 2/38 623/20.32 |
| 2011/0218541 A1 | 9/2011 | Bailey et al. | |
| 2011/0307067 A1 | 12/2011 | Dees | |
| 2012/0089234 A1 | 4/2012 | Mouillet et al. | |
| 2012/0185053 A1* | 7/2012 | Berger | A61F 2/30734 623/20.16 |
| 2012/0203350 A1 | 8/2012 | Hagen et al. | |
| 2012/0310362 A1 | 12/2012 | Li et al. | |
| 2012/0323334 A1 | 12/2012 | Jones et al. | |
| 2012/0323335 A1 | 12/2012 | Parisi et al. | |
| 2012/0323336 A1 | 12/2012 | Parisi et al. | |
| 2012/0323337 A1 | 12/2012 | Parisi et al. | |
| 2012/0330319 A1 | 12/2012 | Birkbeck et al. | |
| 2013/0006370 A1 | 1/2013 | Wogornan et al. | |
| 2013/0006371 A1 | 1/2013 | Wogornan et al. | |
| 2013/0006376 A1 | 1/2013 | Wogornan et al. | |
| 2013/0006378 A1 | 1/2013 | Wogoman | |
| 2013/0024001 A1 | 1/2013 | Wentorf et al. | |
| 2013/0035765 A1 | 2/2013 | Dacus | |
| 2013/0197653 A1 | 8/2013 | Hawkins et al. | |
| 2013/0204380 A1 | 8/2013 | Mouillet et al. | |
| 2013/0211532 A1 | 8/2013 | Samuelson et al. | |
| 2013/0218284 A1* | 8/2013 | Eickmann | A61F 2/389 623/20.32 |
| 2013/0226305 A1 | 8/2013 | Donno et al. | |
| 2013/0227854 A1 | 9/2013 | Zhang et al. | |
| 2013/0345821 A1 | 12/2013 | Jones et al. | |
| 2014/0018932 A1 | 1/2014 | McMahon | |
| 2014/0025081 A1 | 1/2014 | Lorio et al. | |
| 2014/0128973 A1 | 5/2014 | Howard et al. | |
| 2014/0142713 A1 | 5/2014 | Wright et al. | |
| 2014/0228851 A1 | 8/2014 | Guloy, Jr. et al. | |
| 2015/0045801 A1 | 2/2015 | Axelson, Jr. et al. | |
| 2015/0081031 A1 | 3/2015 | Parisi et al. | |
| 2015/0196366 A1 | 7/2015 | Kirn et al. | |
| 2015/0265410 A1 | 9/2015 | Parisi et al. | |
| 2015/0374500 A1 | 12/2015 | Donno et al. | |
| 2016/0030053 A1 | 2/2016 | Yager et al. | |
| 2016/0220379 A1 | 8/2016 | Parisi et al. | |
| 2016/0270856 A1 | 9/2016 | Park et al. | |
| 2016/0278873 A1 | 9/2016 | Fisher et al. | |
| 2017/0086982 A1 | 3/2017 | Yager | |
| 2017/0156872 A1 | 6/2017 | Earl et al. | |
| 2017/0189193 A1 | 7/2017 | Parisi et al. | |
| 2018/0064543 A1 | 3/2018 | Wright et al. | |
| 2018/0092746 A1 | 4/2018 | Donno et al. | |
| 2018/0125584 A1 | 5/2018 | Lang | |
| 2018/0140440 A1 | 5/2018 | Jackson et al. | |
| 2019/0046215 A1 | 2/2019 | Yager et al. | |
| 2019/0046323 A1 | 2/2019 | Yager | |
| 2020/0222198 A1 | 7/2020 | Yager | |

FOREIGN PATENT DOCUMENTS

| | | | | |
|---|---|---|---|---|
| CN | 102006840 A | 4/2011 | | |
| EP | 0376658 | 7/1990 | | |
| EP | 0546726 | 11/1992 | | |
| EP | 0567705 | 3/1993 | | |
| EP | 1354571 | 10/2003 | | |
| EP | 1477142 | 12/2004 | | |
| EP | 1862150 | 12/2007 | | |
| EP | 2702962 A1 | 5/2014 | | |
| FR | 3008605 | 1/2015 | | |
| JP | 3469972 | 11/2003 | | |
| JP | 3495161 | 2/2004 | | |
| JP | 2004166802 | 6/2004 | | |
| WO | 9014806 | 12/1990 | | |
| WO | 9014806 A1 | 12/1990 | | |
| WO | 9535074 A1 | 12/1995 | | |
| WO | 9603939 A1 | 2/1996 | | |
| WO | 0023010 | 4/2000 | | |
| WO | 2004016204 | 2/2004 | | |
| WO | 2005122967 | 12/2005 | | |
| WO | 2009105495 A1 | 8/2009 | | |
| WO | 2010008803 A2 | 1/2010 | | |
| WO | 2010075365 A2 | 7/2010 | | |
| WO | 2010108550 A1 | 9/2010 | | |
| WO | 2011072235 A2 | 6/2011 | | |
| WO | 2012031774 A1 | 3/2012 | | |
| WO | 2012112698 A2 | 8/2012 | | |
| WO | 2012173704 A1 | 12/2012 | | |
| WO | 2012173706 A1 | 12/2012 | | |
| WO | 2012173740 A1 | 12/2012 | | |
| WO | 2016153927 A1 | 9/2016 | | |
| WO | 2017058535 A1 | 4/2017 | | |
| WO | WO-2021022047 A1 * | 2/2021 | | A61F 2/30721 |

OTHER PUBLICATIONS

Storer, John, International Search Report for Int'l App. No. PCT/US2022/079430, Mar. 30, 2023, European Patent Office, Rijswijk, Netherlands.

Storer, John, Communication Pursuant to Article 94(3) EPC., Apr. 22, 2025, European Patent Office, Munich, Germany.

* cited by examiner 70
180 - gθ
P
75
76
78
74
84
89c1
85
gθ
GLA
81
89a1
71
A
θ
kh
73
KLA
gh
δ
77

89c
89d
89a
89b
89d1
83
L
89b1
gδ
180 - gδ
M

TIBIAL COMPONENT OF ENDOPROSTHETIC KNEE IMPLANT, KITS AND INSTRUMENTS THEREFORE, AND METHODS OF USE

1. REFERENCE TO RELATED APPLICATION

This application claims the benefit of priority to U.S. Provisional Application No. 63/264,332 filed on Nov. 19, 2021. The disclosure of this related application is hereby incorporated into this disclosure in its entirety.

BACKGROUND OF THE INVENTION

2. Technical Field

The present disclosure relates generally to the field of knee implants, and more particularly to tibial components for endoprosthetic knee implants adapted for kinematic alignment, anatomic alignment, and methods of implantation thereof.

3. Related Art

Knee arthroplasties are procedures in which an orthopedic surgeon replaces portions of severely diseased knee joints with an artificial endoprosthetic implant that is intended to restore joint function and alleviate pain. The procedure itself generally consists of the surgeon making a vertical midline anterior incision on the bent knee (i.e., a knee in flexion). The surgeon then continues to incise tissue to access the joint capsule. Once pierced, the patella is retracted and the distal condyles of the femur, the cartilaginous meniscus, and the proximal tibial plateau are exposed.

The surgeon then removes the cartilaginous meniscus and may use instrumentation to measure and resect the distal femur and the proximal tibia to accommodate the endoprosthetic knee implant. The endoprosthetic knee implant generally comprises three primary components: a femoral component, a tibial component, and a meniscal insert component that is disposed between the installed femoral and tibial components.

The resections themselves often remove areas of diseased bone. These resections also necessarily modify the profiles of the remaining distal femur and proximal tibia to better accommodate complementary shapes of the associated implant component. That is, the resected distal femur will eventually fit into a complementary femoral component. Likewise, the resected proximal tibia will eventually support a complementary tibial component.

The tibial component of the endoprosthetic implant typically includes a unitary keel descending downwardly and perpendicularly from a lower surface of a tibial base plate. When installed on the resected proximal tibia, the keel extends into a bore in the intramedullary canal of the tibia. The keel of an installed tibial component can be thought of as being disposed in a coronal plane and is oriented perpendicularly to the lower surface of the tibial base plate.

In the field of knee arthroplasties, there are several schools of thought concerning the angles at which resection of the distal femoral condyles and the proximal tibia should be made. The angles of resection largely determine how the implant components will sit in the joint and can influence how the artificial joint performs over time.

One school of thought is the anatomic alignment method. In the anatomic alignment method, the surgeon resects the tibia at 3 degrees of varus because this is believed to be the average angle of the native joint line. Femoral resections and ligament releases are then performed to keep a straight hip-knee-ankle axis of the limb.

Another school of thought is the mechanical alignment method. The priority in mechanical alignment is to resect the tibia perpendicular to the length or axis of the tibial shaft (i.e., parallel to the transverse body plane). A mechanically resected tibial plateau would have a 0 degree varus tilt. The distal femur is then adjusted to account for the 0 degree varus tilt of the resected tibia and any necessary ligament releases are performed to maintain a straight hip-knee-ankle axis.

By contrast, with the kinematic alignment method, the surgeon seeks to restore the patient's specific natural pre-diseased joint line based on data made available to the surgeon both pre-operatively and intra-operatively. Most kinematic alignment techniques start with referencing the distal femur and generally adjusting the slope of the tibial resections to be parallel to the distal femoral resection when the knee is in extension, and parallel to the posterior resections of the femoral condyles when the knee is in flexion.

The utility of traditional tibial components can be severely limited when the proximal tibia is resected at an angle. On average, a unitary tibial component may have a keel having a length in the range of about 35 millimeters ("mm") to about 65 mm. When the tibial base plate is disposed at an angle on the resected tibia, the keel is likewise disposed at an angle relative to the longitudinal axis of the operative tibia. If the angle of the tibial resection is too great, or if the keel is too long, the keel will abut the medial or lateral inner cortical wall of the tibia. In extreme cases, repeated pressure of the keel on the inner cortical wall could weaken or penetrate the cortex (i.e., the compact, generally non-spongy outer wall of the bone).

Shortening the keel excessively is usually not possible. A shortened keel risks ineffective force transfer from the knee into the tibia during normal use. This thereby increases the risk that the tibial component may become unseated during normal activity.

The problem of having the keel abut the inner cortical wall is particularly pronounced in revision or trauma cases. In such cases, the surgeon typically resects more of the proximal tibia to expose heathy bone. For context, in revision cases, the prior-installed implant is usually cemented to the tibia. The surgeon removes the prior-installed implant by resecting the underlying bone. As a result, there is often less healthy bone available for the surgeon to work with after the prior-installed implant has been removed. In trauma cases, complex fractures may encourage resecting the tibial below the complex fracture area to simplify reconstruction. However, the tibia tapers distally. This causes a narrowing of the intramedullary canal (particularly in the metaphysis and diaphysis) and of the abutting inner cortical walls. Stated simply, with available tibial components, the more that the surgeon resects the proximal tibia, the less room the surgeon has when setting the resection angle of the tibia. If the angle it too steep, the keel of the tibial component will abut or penetrate the tibial cortex.

To avoid this problem, surgeons may choose to resect the tibia at 0 degrees varus and proceed with a mechanical alignment procedure. The mechanical alignment technique can provide good stability when the patient's leg is in extension (e.g., when the patient is standing), but the implants that are commonly used with this technique often require the release of the anterior cruciate ligament ("ACL"). In some circumstances, the posterior cruciate ligament ("PCL") may also be released. The ACL normally prevents the tibia from sliding too far anteriorly and from rotating too far relative to the femur. The absence of either of these ligaments can lead to feelings of weakness when the leg is in flexion. Furthermore, changing the location of the patient's natural joint line can lead to feelings of discomfort. Patients who alter their gait to accommodate the new joint line may chronically stress the remaining muscles, which can further exacerbate the feelings of discomfort and contribute to additional musculoskeletal problems in the future.

SUMMARY OF THE INVENTION

The problem of the limited range of motion for tibial components of endoprosthetic knee implants in situations in which the proximal tibia is resected at an angle relative to a transverse plane is mitigated by a tibial component of an endoprosthetic knee implant comprising: a tibial baseplate; and a keel extending from a lower surface of the tibial baseplate, wherein a keel axis extends axially through the keel, wherein the tibial baseplate is disposed at a keel posterior angle relative to the keel axis, and wherein the tibial baseplate is disposed at a keel varus angle relative to the keel axis.

In these and other situations, it would be advantageous to have a tibial component of an endoprosthetic knee implant that is configured to provide a built-in varus tilt (i.e., keel varus angle) and a built-in posterior slope (i.e., keel posterior angle).

It would therefore be unique and advantageous to have tibial component of an endoprosthetic knee implant that is adapted to kinematic and/or anatomic knee arthroplasty techniques having the characteristics and features described herein.

It is contemplated that certain exemplary embodiments in accordance with the present disclosure may provide tibial components of endoprosthetic knee implants that are particularly adapted for use in kinematic or anatomic knee arthroplasty procedures.

It is further contemplated that certain exemplary embodiments in accordance with the present disclosure can include exemplary instruments for surgically installing exemplary tibial components of an endoprosthetic knee implants that are particularly adapted for use in kinematic or anatomic knee arthroplasty procedures.

It is still further contemplated that certain exemplary embodiments in accordance with the present disclosure can include kits comprising the exemplary tibial components, exemplary instruments therefore, or a combination thereof.

It is still further contemplated that the exemplary tibial components, instruments therefore, and kits thereof may be useful in revision procedures and primary procedures and of the primary procedures, particularly in stemmed primary procedures.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

DETAILED DESCRIPTION OF THE PREFERRED EMBODIMENTS

Figure 1A:
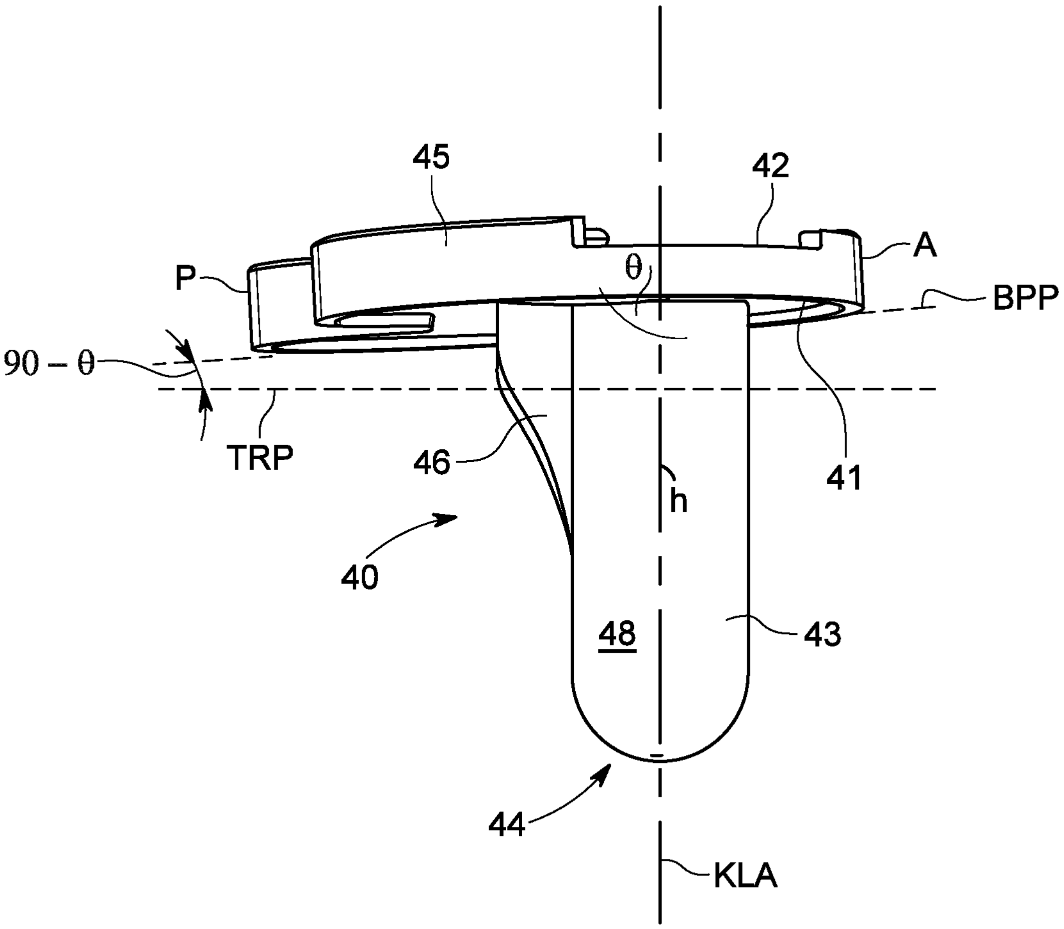
FIG. 1A is a side view of an exemplary embodiment of a tibial component of an endoprosthetic knee implant, featuring a right knee unitary tibial component comprising a base having a varus tilt and a posterior slope relative to the keel.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar or the same reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any subranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and, "lower" are relative to each other in location, i.e., an upper component is located at a higher elevation than a lower component in each orientation, but these terms can change if the orientation is flipped.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other.

Throughout this disclosure, various positional terms, such as "distal," "proximal," "medial," "lateral," "anterior," and "posterior," will be used in the customary manner when referring to the human anatomy. More specifically, "distal" refers to the area away from the point of attachment to the body, while "proximal" refers to the area near the point of attachment to the body. For example, the distal femur refers to the portion of the femur near the tibia, whereas the proximal femur refers to the portion of the femur near the hip. The terms, "medial" and "lateral" are also essentially opposites. "Medial" refers to something that is disposed closer to the middle of the body. "Lateral" means that something is disposed closer to the right side or the left side of the body than to the middle of the body. Regarding "anterior" and "posterior," "anterior" refers to something disposed closer to the front of the body, whereas "posterior" refers to something disposed closer to the rear of the body."

However, when referring to any component of the exemplary endoprosthetic implant or instruments described herein (e.g., an exemplary tibial component), particularly when such components are in an uninstalled or unassembled configuration, the various positional terms such as "distal," "proximal," "medial," "lateral," "anterior," and "posterior," absolute terms that refer to the associated position depicted in the accompanying figures and that do not change relative to the component's orientation is space. For example, a "proximal end" of a modular keel refers to the end indicated in the accompanying figures regardless of the orientation such "proximal end" relative to a reference (e.g., a person or the surface of the Earth).

"Varus" and "valgus" are broad terms and include without limitation, rotational movement in a medial and/or lateral direction relative to the knee joint.

The phrase, "mechanical axis of the femur" refers to an imaginary line drawn from the center of the femoral head to the center of the distal femur at the knee.

The phrase, "mechanical axis of the tibia" refers to an imaginary line drawn from the center of the proximal tibia to the center of the distal tibia, which is just above the ankle.

The term, "anatomic axis" refers to an imaginary line drawn lengthwise down the middle of femoral shaft or tibial shaft, depending upon use. The mechanical axis of the tibia and the anatomic axis of the tibia are generally considered to be co-linear.

Figure 6:
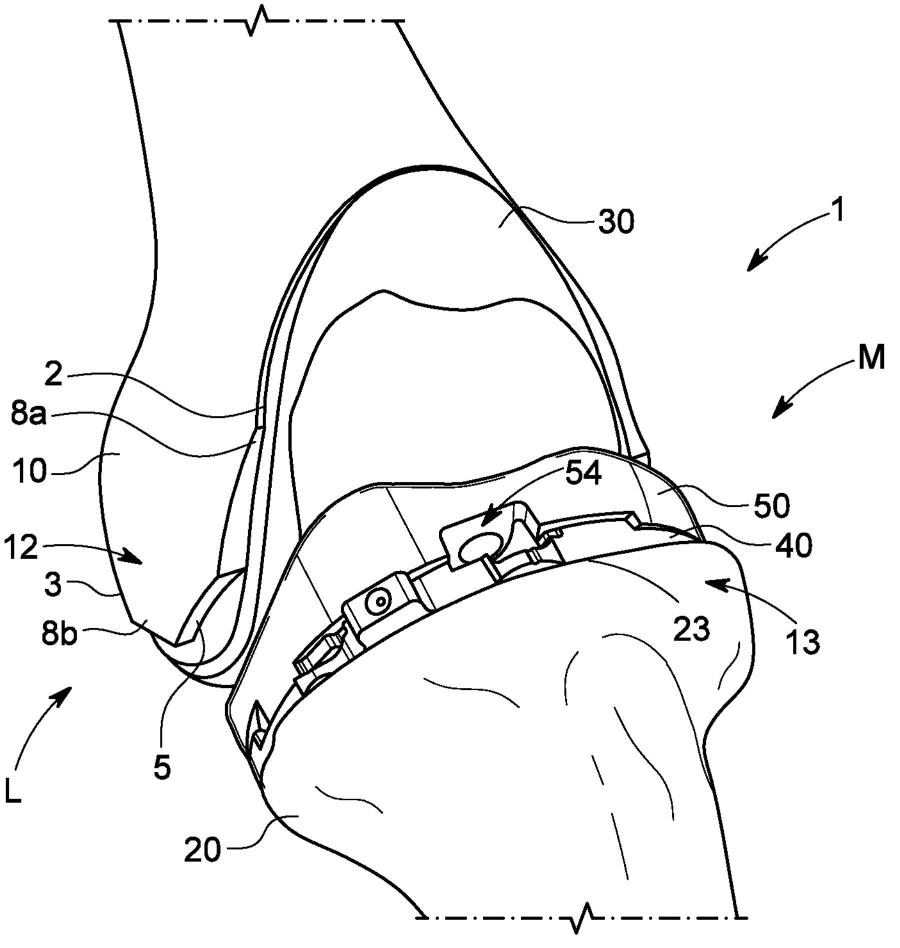
FIG. 6 shows an example endoprosthetic knee implant installed on a resected distal femur and a resected proximal tibia.

Referring to FIG. 6, an example endoprosthetic knee implant 1 is depicted installed on a resected distal end 12 of a femur 10 and on the resected proximal end 13 of the tibia 20. Unless otherwise stated, "endoprosthetic knee implant" can refer to either a trial implant, such as the one depicted in FIG. 6, or an actual endoprosthetic knee implant that is designed to be surgically implanted into the patient and used as an artificial joint for an extended period. The endoprosthetic knee implant 1 generally comprises: a femoral component 30 configured to be engaged to the resected distal end 12 of the femur 10, a tibial component 40 configured to be engaged to the resected proximal end 13 of the tibia 20, and a meniscal insert 50, which is disposed between the femoral component 30 and the tibial component 40 when installed in the patient.

To initiate a typical revision knee arthroplasty, the surgeon makes a vertical midline incision on the anterior side of the operative knee. The incision is generally made with the knee in flexion at or below the tibial tuberosity and may extend several inches above the patella.

In a primary knee arthroplasty, the surgeon then continues to incise the fatty tissue to expose the anterior aspect of the joint capsule. The surgeon may then perform a medial parapatellar arthrotomy to pierce the joint capsule and resect the medial patellar retinaculum. A retractor is then commonly used to move the patella generally laterally to expose the distal condyles of the femur and the cartilaginous meniscus resting on the proximal tibial plateau. The surgeon then removes the meniscus and uses instrumentation to measure and resect the distal femur and proximal tibia to accommodate trial implants. Trial implants are test endoprostheses that generally have the same functional dimensions of the actual endoprostheses, but trial implants are designed to be temporarily installed and removed for the purposes of evaluating the fit of the actual endoprostheses and for the purposes of evaluating the knee joint's kinematics. The surgeon removes the trial implants and installs the actual implants once the surgeon is satisfied with the trial implant's sizing and the knee joint's kinematics.

Measurement and installation methods differ. Surgeons generally execute a mechanical alignment, anatomic alignment, or kinematic alignment technique according to preference, patient anatomy, the state of the operative joint, and available instruments.

To highlight the kinematic alignment technique and by way of example, a surgeon may proceed as described in U.S. Pat. No. 11,246,603 to Steensen et. al. The principle of kinematic alignment is that the surgeon uses instrumentation and implants to ascertain and restore the patient's natural pre-diseased joint line. The instruments described in U.S. Pat. No. 11,246,603 solve several issues encountered in kinematic techniques, such as allowing: the angle of the current or natural joint surface to be measured on both the femur and tibia; a wear factor to be used so that the measured amount of bone resection restores the joint surface to its pre-diseased level on both the femur and tibia; the surgeon to resect a specific amount of bone from the medial and lateral aspects of the joint surface on both the femur and tibia; the surgeon to visualize the angle of resection; the angle of resection to float infinitely, rather than in specific increments (within an acceptable range on both the femur and tibia); the surgeon to selectively lock the angle if desired; and the surgeon to measure the resection of the medial and lateral femoral condyles or of the medial and lateral tibial hemi-plateaus.

To summarize the distal resection step, the surgeon may ascertain the amount of cartilage wear on the distal condyles of the femur, attach a movable resection guide instrument to the exposed distal femur, and adjust the resection guide instrument to account for the measured loss of articular cartilage and the size of the implant. For example, if the implant is 10 mm in size and if the surgeon measures 2 mm of missing cartilage on the medial distal femoral condyle and 1 mm of missing cartilage on the lateral femoral condyle, the surgeon can adjust the resection guide instrument to position a resection slot to resect 8 mm of bone on the medial condyle and 9 mm of bone of the lateral condyle. The surgeon then inserts a saw or other cutting instrument through the resection slot to create the distal resection surface 5 at the desired angle and location.

By resecting the distal femur at this angle, the surgeon creates the first mating surface for the femoral component at an angle that is consistent with the angle of the patient's natural pre-diseased joint line when the knee is in extension (i.e., as depicted in FIG. 6). The 8 mm of resection on the medial side plus the 2 mm of measured cartilage loss thereby is sized to accommodate a 10 mm endoprosthetic implant 1 on the medial side M. Likewise, the 9 mm resection of the lateral side plus the 1 mm of measured cartilage loss is thereby sized to accommodate the 10 mm endoprosthetic implant 1 on the lateral side L.

The surgeon may then place the knee in flexion (i.e., bend the knee) and repeat the measurement and resection process to create the posterior resection surface 3.

After creating the distal resection surface 5 and possibly the posterior resection surface 3, the surgeon may place a four-in-one cutting block (or separate resection guides) on the distal resection surface 5 to create the chamfer resection surfaces **8*a*, 8*b*, the anterior resection surface 2, and the posterior resection surface 3 if not made previously. The femoral component 30 has complementary faces that are disposed against the respective resection surfaces 5, 8*a*, 8*b*, 2, and 3 when the femoral component 30 is disposed in an installed configuration as shown in FIG. 6**.

It will be appreciated that the presence of the respective resection surfaces 5, **8*a*, 8*b*, 2, and 3 and the complementary mating faces of the femoral component 30 are the primary means by which the femoral component 30 is "configured to be engaged" to the resected distal end 12 of the femur 10. It will be further appreciated that the engagement side of the femoral component 30 may further comprise one or more projections (e.g., spikes) designed to be inserted into any one of the resection surfaces 5, 8*a*, 8*b*, 2, and 3 to further facilitate the engagement of the femoral component 30 to the resected distal end 12 of the femur 10**. By way of further example, press-fit femoral components typically have a porous roughened surface on the engagement side. The porous surface permits regrowth of the bone into these pours over time.

Surgeons can also apply biocompatible "bone cement" to help secure the femoral component 30 to the resected distal end 12 of the femur 10. It will be appreciated that "bone cement" is a term of art used by people in the orthopedic industry even though bone cements themselves generally do not have adhesive properties. Bone cements generally rely on a close mechanical interlock between the irregular surface of the bone and the surface of the connective side of the endoprosthesis. Bone cements may or may not be laden with antibiotics depending upon the intended use. Common bone cements include polymethyl methacrylate ("PMMA"), calcium phosphate cements ("CPCs"), and glass polyalkenoate isomer cements ("GPICs") . It will be appreciated that when present, the use of projections, porous roughened surfaces, and/or "bone cement" to further facilitate engaging the femoral component 30 to the distal end 12 of the femur 10 and can therefore also fall within the scope of the "femoral component 30 configured to be engaged to the resected distal end 12 of the femur 10" language. Bone cement is difficult to remove once cured. Bone cement's presence is a significant factor that contributes to the need to resect the supportive bone in revision procedures.

Creating the resected proximal end 13 of the tibia 20 can be completed before or after the femur 10 is resected. A cutting guide is typically placed on the anterior surface of the tibia 20, and the surgeon can adjust the varus and valgus angle of resection and optionally the posterior slope of resection depending upon the elected knee alignment method (e.g., anatomic, mechanical, or kinematic). Once the resection angle is set, the surgeon inserts a saw or other cutting instrument through a resection slot in the tibia resection guide to create the resected tibial surface 23. For example, in a kinematic operation, the tibial longitudinal axis LA (i.e., a projected stem axis) is determined and the tibia 20 is resected relative to the tibial longitudinal axis LA. The tibia 20 is resected at a varus tilt 90 -δ sloping down from the lateral L to the medial M side, commonly at about three degrees relative to the keel longitudinal axis KLA. The tibia is further resected at a posterior slope 90-θ that slopes down from the anterior side A to the posterior side P of the patient's tibia 20, commonly at about three degrees relative to the keel longitudinal axis KLA. The surgeon may then use the exemplary punch guide 83 described further below to insert a reamer and/or punch (see 73, FIG. 9) into the exposed epiphysis or metaphysis of the exposed intramedullary canal of the resected tibial surface 23 to create a cavity. This cavity can be desirably sized to accommodate the keel 43 (FIG. 1A) of the tibial component 40.

The keel 43 is then inserted into the cavity (see FIG. 2B) and the surgeon may hammer the tibial component 40 into place such that the lower surface 41 of the baseplate 45 rests upon the resected proximal end 13 of the tibia 20 (i.e., on the resected tibial surface 23). In this manner, the tibial component 40 can be said to be "configured to be engaged" to the resected proximal end 13 of the tibia 20. As with the femoral component, the lower surface 41 of the baseplate 45 may comprise projections (e.g., spikes) in certain embodiments. By way of further example, press-fit tibial components typically have a porous roughened surface on the engagement side. The porous surface permits regrowth of the bone into these pours over time. In certain applications, the surgeon may elect to place bone cement between the resected tibial surface 23 and the lower surface 41 of the baseplate 45. When present, the projections, porous roughened surface, and/or the use of bone cement as described can fall within the scope of the "tibial component 40 configured to be engaged to the resected proximal end 13 of the tibia 20" language.

In a revision procedure (i.e., a subsequent knee arthroplasty in which the surgeon removes and replaces a prior installed endoprosthetic knee implant), the surgeon may release scar tissue around the patellar tendon after the surgeon has performed the initial incision. The surgeon can then move (i.e., preform a subluxation of) the patella or patellar implant generally laterally to expose the prior-installed implant, which usually has a femoral component installed on the distal femur, a tibial component installed on the proximal tibia, and a meniscal insert disposed between the femoral component and the tibial component. The surgeon then removes the prior-installed implant.

It will be appreciated that the type of prior-installed implant can vary from case to case. Prior-installed implants can include static spacers that have been inserted into aligned intramedullary bores in the distal femur and proximal tibia to immobilize the knee joint, or complex implants that have been used to reconstruct portions of the knee joint that had undergone trauma. However, common prior-installed implants include implants installed during a primary total or partial knee arthroplasty, or prior revision implants.

Removal of the prior-installed implants generally involves cutting away the bone underlying the bone cement—or in the case of press-fit implants, the bone underlying the press-fit implant. This resection exposes fresh bone capable of receiving a revision press-fit or bone cement bondable implant. Removing bone to remove the prior-installed implant would move the joint line if the revision implant was not sized to replace the newly resected bone.

Figure 2A:
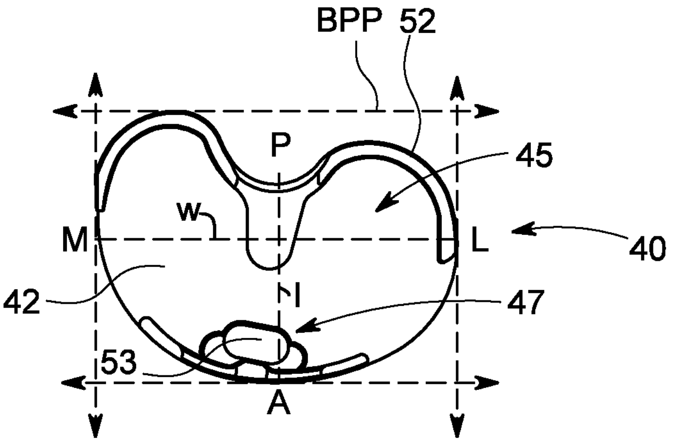
FIG. 2A is a top view of an exemplary embodiment of a left sided tibial component of an endoprosthetic knee implant, featuring a left knee unitary tibial component comprising a base having a varus tilt and a posterior slope relative to the keel.
Figure 2B:
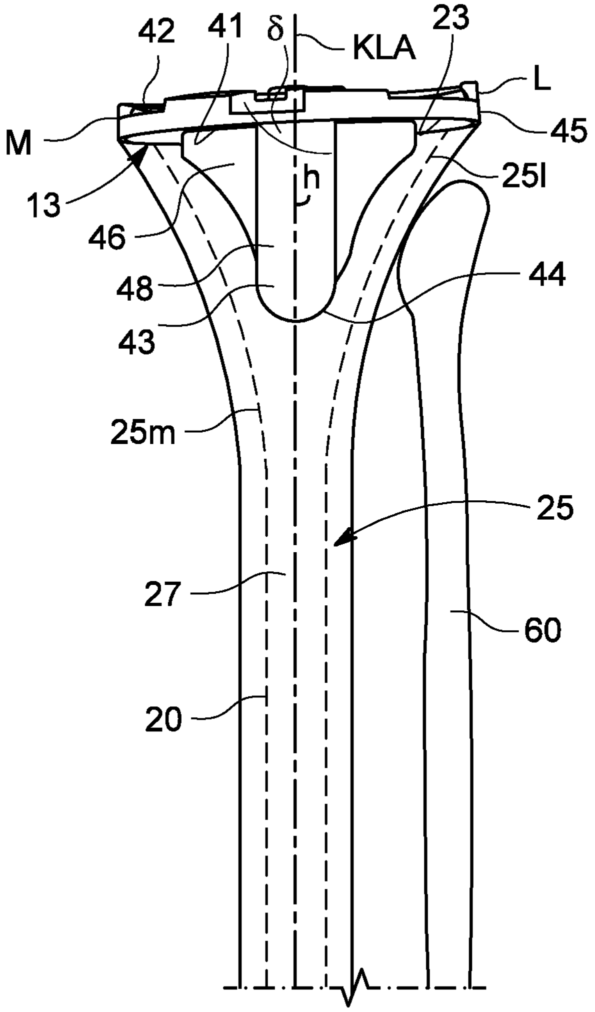
FIG. 2B is a front view of the exemplary tibial component of FIG. 2A shown implanted on and in a resected tibia. The resected tibia is shown in cross-section.

FIG. 2B is an anterior view of an exemplary tibial component 40 disposed in a resected tibia 20. The resected tibia 20 is shown in cross section. The exemplary tibial component 40 generally comprises a baseplate 45 having an upper surface 42 that is distally disposed from a lower surface 41 and an anterior side A that is distally disposed to a posterior side P (see FIG. 2A). The baseplate 45 has a medial side M distally disposed from a lateral side L. A medial-lateral line M-L can be imagined to extend from the medial side M directly across the baseplate 45 (and horizontally when viewed in the orientation depicted in FIG. 2A) to the lateral side L of the baseplate 45. Likewise, an anterior-posterior line A-P can be imagined to extend from the anterior side A directly across the baseplate 45 (and vertically when viewed in the orientation depicted in FIG. 2A) to the posterior side P of the baseplate 45. The anterior-posterior line A-P is perpendicular to the medial lateral line M-L.

In the depicted embodiment, the resected tibial surface 23 of a given tibia 20 is not perfectly symmetrical. Moreover, the left tibia is chiral to the right tibia. In the depicted embodiment, a given baseplate 45 is typically designed for either the left tibia or the right tibia. The anterior side A, posterior side P, medial side M, and the lateral side L of a given baseplate 45 are desirably sized and shaped to closely approximate the profile (i.e., perimeter) of the resected tibial surface 23 (see FIG. 2A). In other exemplary embodiments, the baseplate 45 can be symmetrical. Such exemplary symmetrical embodiments can be used with the modular keel 43 that is further described with reference to FIGS. 7A-8B below. It is contemplated that in such exemplary embodiments, a symmetrical baseplate 45 can become a subcomponent of a left or right tibial component 40 upon being placed in an assembled configuration together with a left or right modular keel 43. In other exemplary embodiments, the symmetrical tibial baseplate and the keel 43 can be unitary.

In the exemplary embodiments shown in FIGS. 1A-4C, a keel 43 extends downwardly from the lower surface 41 of the baseplate 45. The keel 43 can comprise one or more fins 46 extending outwardly from the keel 43.

In general, the femoral component 30, tibial component 40, and meniscal insert 50 can be made from any biocompatible material designed to withstand the stress of repeated and normal use of the knee. In practice, the femoral component 30 and tibial component 40 are frequently made from cobalt-chromium alloys, titanium, titanium alloys, zirconium, zirconium alloys, nickel, or nickel alloys. In certain embodiments, these components, particularly the femoral component 30, may have a ceramic coating (or may comprise an outer ceramic layer) on the articular surface. In other embodiments, the entire femoral component 30 can be made from ceramic. In still other embodiments, the entire tibial component 40 can be made from ceramic. The meniscal insert 50 is typically made from ultra-high molecular weight polyethylene ("UHMWPE") or from a ceramic.

Figure 5:
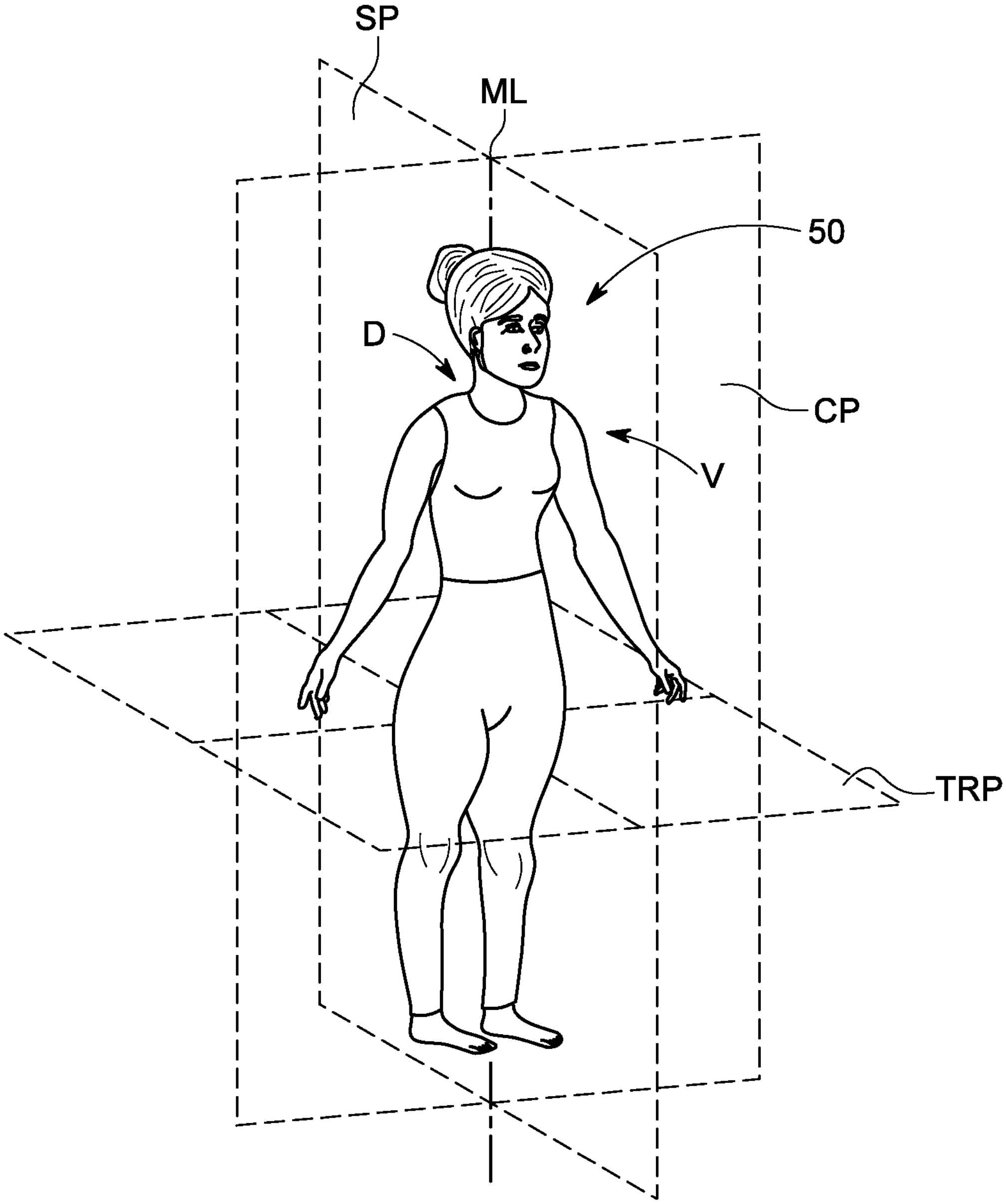
FIG. 5 is a perspective view of a person used to illustrate a transverse plane, coronal plane, and sagittal plane.

Reference is made to FIG. 5, which illustrates three standard anatomical body planes commonly used in reference to human anatomy. The coronal plane CP or frontal plane is any imaginary vertical plane that divides the body 50 into a ventral section V and a dorsal section D. Although FIG. 5 depicts the coronal plane CP intersecting the midline ML of the body 50, it will be understood that the coronal plane CP can be imagined at any vertical location through the body 50 provided that the coronal plane CP divides the body 50 into a ventral section V and a dorsal section D. The sagittal plane SP, or longitudinal plane, is an imaginary vertical plane that divides the body 50 into left and right parts. The sagittal plane SP is depicted as intersecting the body 50 at the midline ML, but it will be understood that a sagittal plane SP can be imagined away from the midline to designate unequal right and left parts. The transverse plane TRP, or axial plane is an imaginary plane that divides the body 50 into superior and inferior parts (i.e., upper, and lower parts). The transverse plane TRP is perpendicular to both the coronal plane CP and the sagittal plane SP. The transverse plane TRP can be imagined to extend generally horizontally from the vertical midline ML of the body 50 at any location along the midline ML provided that the transverse plane TRP divides the body 50 into superior and inferior sections. Reference to these anatomical planes will be used to describe the relationship of certain parts of exemplary embodiments of the present disclosure. It will be appreciated that the exemplary implants described herein do not need to be physically implanted into a patient in order to refer to the anatomical planes.

As shown in FIGS. 1A-4C, exemplary embodiments in accordance with this disclosure can comprise, generally, a tibial component 40 of an endoprosthetic knee implant 1 having a baseplate 45 and a keel 43 extending downwardly from the baseplate 45, wherein the baseplate 45 defines a baseplate plane BPP that is coplanar with the length l and width w of the baseplate 45, wherein the baseplate 45 (and therefore the baseplate plane BPP) is oriented at a compound angle relative to a keel longitudinal axis KLA, the keel longitudinal axis KLA extending lengthwise through the keel 43 (i.e., parallel to the height dimension h of the keel 43), wherein the compound angle can be said to comprise a "keel varus angle" δ and a "keel posterior angle" θ.

For the purposes of this disclosure, a "keel posterior angle" θ is the acute angle defined by the intersection between the anterior-posterior line A-P of the baseplate plane BPP (represented by BPP in FIGS. 1A and 3A) and the keel longitudinal axis KLA, wherein the acute angle is disposed closer to the posterior side P of the keel 43 than the anterior side A. In exemplary embodiments, the keel posterior angle θ is less than 90 degrees and preferably greater than or equal to 75 degrees. It is contemplated that within this provided range, a keel posterior angle θ of or about 87 degrees may be desirable in some embodiments because it is believed that the native pre-diseased joint line for the average patient may be replicated in part by orienting the resected tibial surface 23 at a three degree posterior slope (e.g., 90-θ). However, in other exemplary embodiments, the posterior slope 90-θ can be between greater than zero degrees and less than or equal to about fifteen degrees, depending on surgeon preference and natural anatomy of the patient.

Figure 3A:
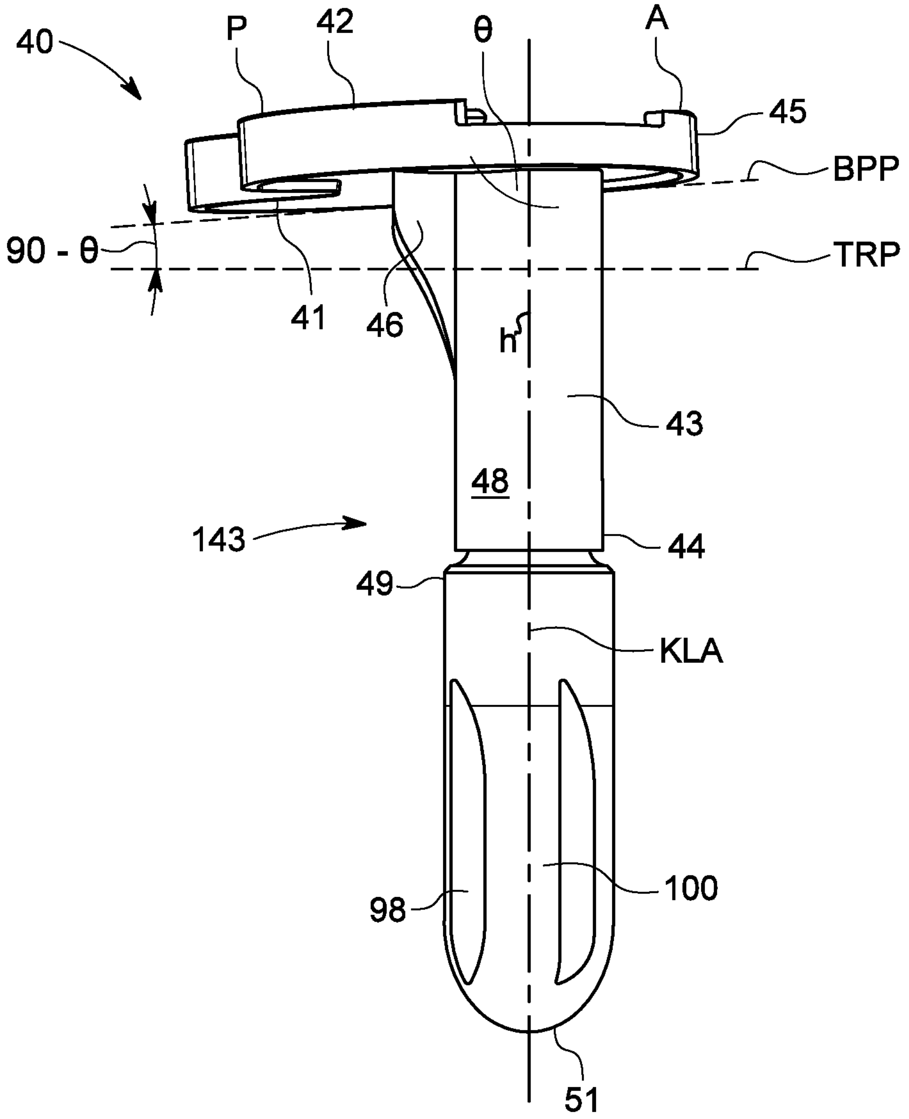
FIG. 3A is a side view of an exemplary embodiment of a tibial component of an endoprosthetic knee implant, featuring a right knee modular tibial component comprising a baseplate having a varus tilt and a posterior slope relative to a transverse plane.

A "posterior slope" in this context is a term of art that typically refers to the anterior to posterior orientation of the resected tibial surface 23. A "posterior slope" is typically thought of as the angle of the anterior-posterior line A-P of the resected tibial surface 23 relative to an intersecting transverse plane TRP. Because the lower surface 41 of the baseplate 45 is desirably disposed on the resected tibial surface 23 and oriented parallel to the resected tibial surface 23 in an installed configuration, the "posterior slope" can also refer to the anterior to posterior orientation of the baseplate 45 of the exemplary tibial components 40 described herein regardless of orientation; however, this relationship is especially pronounced when said baseplate 45 is oriented as it would be in the installed configuration. FIGS. 1A and 3A illustrate this concept by showing the anterior posterior line A-P of the baseplate 45 (represented by the baseplate plane BPP) intersecting a transverse plane TRP at the posterior side P of the baseplate 45. Because the relationship of posterior slope to the keel posterior angle θ is 90 degrees minus θ (where θ is the value of the keel posterior angle) a compound angle that comprises a keel posterior angle θ can necessarily be said to comprise a posterior slope (90-θ).

For the purposes of this disclosure, a "keel varus angle" δ can be described as the acute angle defined by the intersection between the medial lateral line M-L of the baseplate plane BPP (represented by BPP in FIGS. 1C and 3C) and the keel longitudinal axis KLA, wherein the acute angle is disposed closer to the medial side M of the keel 43 than the lateral side L. In exemplary embodiments, the keel varus angle δ is less than 90 degrees and preferably greater than or equal to 83 degrees. It is contemplated that within this provided range, a keel varus angle δ of or about 87 degrees may be desirable in certain embodiments because it is believed that the native pre-diseased joint line for the average patient may be replicated in part by orienting the resected tibial surface 23 at a three degree varus tilt (e.g., 90-δ). However, in other exemplary embodiments, the varus tilt 90-δ can be between greater than zero degrees and less than or equal to about seven degrees, depending on surgeon preference and natural anatomy of the patient.

A "varus tilt" in this context is a term of art that refers to the medial to lateral orientation of the resected tibial surface 23. A "varus tilt" is typically thought of as the angle of the medial-lateral line M-L of the resected tibial surface 23 relative to an intersecting transverse plane TRP. Because the lower surface 41 of the baseplate 45 is desirably disposed on the resected tibial surface 23 and oriented parallel to the resected tibial surface 23 in an installed configuration, the "varus tilt" can also refer to the medial to lateral orientation of the baseplate 45 of the exemplary tibial components 40 described herein regardless of orientation; however, this relationship is especially pronounced when said baseplate 45 is oriented as it would be in the installed configuration. FIGS. 1C and 3C illustrate this concept by showing the medial-lateral line M-L of the baseplate 45 (represented by the baseplate plane BPP) intersecting a transverse plane TRP. Because the relationship of varus tilt to the keel varus angle δ is 90 degrees minus δ (where δ is the value of the keel varus angle) a compound angle that comprises a keel varus angle δ can necessarily be said to comprise a varus tilt (90-δ).

In this manner, the compound angle for the exemplary tibial components 40 described herein can also be said to comprise a posterior slope (90-θ) and a varus tilt (90-δ).

The exemplary tibial component 40 of an endoprosthetic knee implant 1 can be provided in a unitary (i.e., non-modular; unibody; comprising a single piece) embodiment. In other exemplary embodiments, the keel 43 and the baseplate 45 can be modular, as described below.

FIG. 1A shows a side view of one embodiment of an exemplary tibial component of an endoprosthetic knee implant 1 in an uninstalled configuration. The depicted embodiment is unitary or non-modular right knee tibial component 40. It will be appreciated that the exemplary tibial components 40 described herein have an installed configuration (see e.g., FIG. 2B) in which the tibial component 40 is disposed on and in a resected proximal tibia 20, and an uninstalled configuration (see e.g., FIGS. 1A-1C) in which the tibial component 40 is not disposed on and in a resected proximal tibia 20.

The tibial component 40 includes a baseplate 45 (which is also known as a "tibial tray") and a unitary keel 43 extending downwardly from a lower surface 41 of the baseplate 45. The keel 43 can comprise one or more fins 46 extending outwardly from the keel 43. The fins 46 are typically disposed in the transverse plane TRP when the tibial component 40 is in the installed configuration. In exemplary embodiments, the fins 46 can be disposed at a compound angle relative to the baseplate plane BBP, wherein the compound angle comprises a keel posterior angle and a keel varus angle as described herein. In other exemplary embodiments, the fins 46 can be oriented relative to the keel 43 as the fins 46 would be for a mechanically aligned tibial component.

It will be appreciated that the "non-modular" or "unitary" embodiments described herein can refer to tibial components 40 that have been manufactured as a single piece (e.g., by casting, machining, additive manufacturing, etc.) and to tibial components 40 that have been manufactured as separate pieces (e.g., a baseplate portion 45 and keel portion 43) but that are fixedly engaged to each other in a non-readily-removable manner when made available to the surgeon for the operative procedure (for modular embodiments, see FIGS. 7-8). In both modular and unitary systems, the keel 43 is typically sized and configured for use in stabilizing the tibial component 40 on the proximal tibia 20. In modular systems, a proximal end 61 of the keel 43 can be configured to selectively attach to the baseplate 45. In exemplary embodiments of either non-modular or modular embodiments, the distal end 44 of the keel 43 can be configured to selectively attach to distal stem extensions 100 (see FIG. 3C) to further stabilize the tibial component 40 in the tibia 20.

In certain exemplary embodiments, the distal end 44 of the keel 43 is preferably rounded. The rounded distal end 44 reduces the risk of unnecessarily shaving off of proximate cancellous bone and bone marrow during the installation process. In other exemplary embodiments, the distal end 44 of the keel 43 can be substantially straight, wedge shaped, wedge shaped with a rounded end, conical, conical with a rounded end, frustoconical, frustoconical with a rounded end, pyramidal, pyramidal with a rounded end, frustopyramidal, frustopyramidal with a rounded end, or combinations thereof. Shapes that have a generally convex profile are generally preferable to reduce the risk of unnecessarily ablating cancellous bone and bone marrow during the installation process. All shapes having a generally convex profile are considered to be within the scope of this disclosure. An upper surface 42 of the baseplate is configured to selectively secure the meniscal insert 50 to the baseplate 45. The keel 43 has a keel longitudinal axis KLA extending lengthwise therethrough (i.e., the keel longitudinal axis KLA is disposed parallel to the height h dimension of the keel 43). Unlike prior tibial components 40, the baseplate 45 is not oriented perpendicular to the keel 43 but is instead oriented at a compound angle comprising a keel posterior angle θ and a keel varus angle δ. Without being bound by theory, it is thought that such embodiments can assist in kinematic or anatomic alignment procedures. Moreover, it is contemplated that use of the exemplary tibial components 40 described herein may permit a surgeon to use kinematic alignment or anatomic alignment procedures in revision knee arthroplasties that might not otherwise have been possible using conventional tibial components.

As can be seen in the side view of FIG. 1A, the baseplate 45 slopes downwardly from the anterior side A to the posterior side P of the tibial component 40 relative to the keel longitudinal axis KLS. A baseplate plane BPP can be imagined to be coplanar with the anterior-posterior line A-P and the medial-lateral line M-L (FIG. 1B) of the baseplate 45 (stated differently, the baseplate plane BPP can be imagined to be coplanar with a width w dimension and a length l dimension of the baseplate 45). Because the baseplate plane BPP is co-planar with the anterior-posterior line A-P and the medial-lateral line M-L of the baseplate 45, the baseplate plane BPP can be described as having an anterior-posterior line A-P and a medial-lateral line M-L that are co-linear with the respective anterior-posterior line A-P and medial-lateral line M-L of the baseplate 45. When measured with reference to the keel longitudinal axis KLA, the keel posterior angle θ can be described as the acute angle defined by the intersection between the anterior-posterior line A-P of the baseplate plane BPP (represented by BPP in FIG. 1A) and the keel longitudinal axis KLA, wherein the acute angle is disposed closer to the posterior side P of the keel 43 than the anterior side A.

Stated differently, the intersection of the anterior-posterior line A-P line of the baseplate plane BPP and a transverse plane TRP defines a posterior slope (90-θ).

The transverse plane TRP can be imagined to be disposed perpendicular to the keel longitudinal axis KLA of the keel 43 in both the coronal plane CP (FIG. 5) and the sagittal plane SP (FIG. 5). In exemplary embodiments, the posterior slope 90-θ may be in a range of greater than zero degrees to less than or equal to 15 degrees, preferably between 1 degree and ten degrees. However, in many applications, the posterior slope 90-θ is set at about three degrees.

Figure 1B:
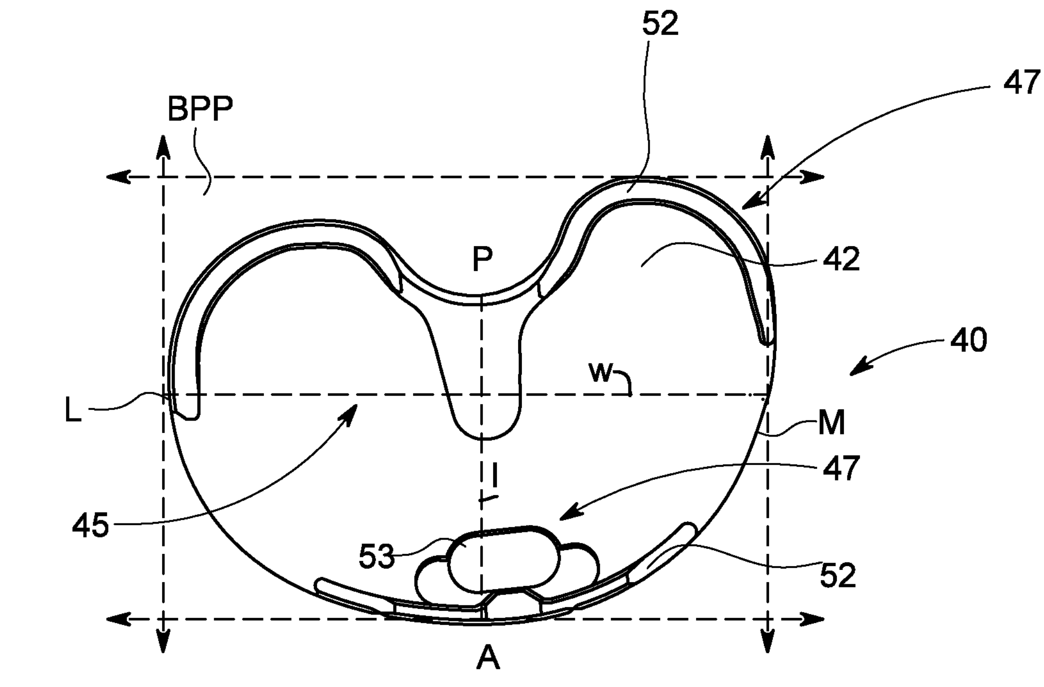
FIG. 1B is a top view of the exemplary tibial component of FIG. 1A.
Figure 1C:
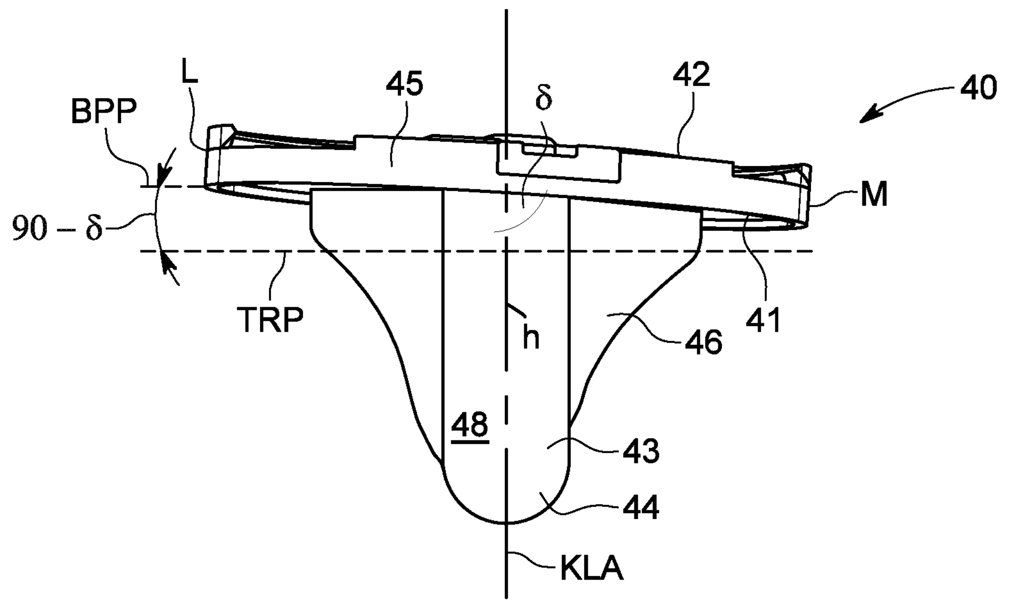
FIG. 1C is a front view of the exemplary tibial component of FIG. 1A.

FIG. 1B shows a top down view of an exemplary tibial component 40. Locking features 47 are shown on the upper surface 42 of the tibial baseplate 45 for reference. In embodiments, the locking features 47 can comprise a partial perimeter lip 52 that can be disposed at the anterior side A of the baseplate 45, at the posterior side P, and partially at the lateral side L and the medial side M. These locking features can also comprise a keying element 53 that can be inserted into (or receive, depending upon configuration) a complementary keying element 54 (FIG. 6) in the meniscal insert 50. In this manner, these locking features 47 mate with complementary locking features (see 54) on the meniscal insert 50 when the meniscal insert 50 is installed on the upper surface 42 of the tibial baseplate 45. As such, the upper surface 42 of the baseplate 45 can be said to be "configured to selectively secure" the meniscal insert 50 to the baseplate 45.

FIG. 1C is a frontal view (i.e., an A-P view) of the tibial component 40. As FIG. 1C more clearly illustrates, the tibial baseplate 45 slopes downwardly from the lateral side L to the medial side M of the tibial component 40 relative to the keel longitudinal axis KLA. Because the baseplate plane BPP is co-planar with the anterior-posterior line A-P and the medial-lateral line M-L of the baseplate 45, the baseplate plane BPP can be described as having an anterior-posterior line A-P and a medial-lateral line M-L that are co-linear with the respective anterior-posterior line A-P and medial-lateral line M-L of the baseplate 45. When measured with reference to the keel longitudinal axis KLA, the keel varus angle δ can be described as the acute angle defined by the intersection between the medial-lateral line M-L of the baseplate plane BPP (represented by BPP in FIG. 1C) and the keel longitudinal axis KLA, wherein the acute angle is disposed closer to the medial side M of the keel 43 than the lateral side L.

Stated differently, the medial-lateral line M-L of the baseplate plane BPP intersects the transverse plane TRP at the medial side M to define a varus tilt 90-δ. The varus tilte 90-δ may be greater than zero degrees to less than or equal to seven degrees. However, in many applications, the varus tilt 90-δ is set at about three degrees. It will be appreciated that tibial components 40 having different combinations of preset keel varus angles δ and keel posterior angles θ (and therefore corresponding present varus tilts 90-δ and posterior slopes 90-θ) are considered to be within the scope of this disclosure.

FIG. 2A is a top down view of one embodiment of an exemplary tibial component 40. The tibial component 40 of FIG. 2A is configured for use on a left knee and is therefore a substantially mirror image of the tibial component shown in FIGS. 1A-1C.

FIG. 2B is an anterior view of the exemplary tibial component of FIG. 2A installed in a resected tibia 20 (i.e., the tibial component 40 is in the installed configuration). As shown, the baseplate 45 has a keel varus angle δ and the baseplate 45 also slopes downwardly from the anterior side A to the posterior side P of the knee (i.e., has a keel posterior angle θ, see FIG. 2C). A medial inner cortical wall 25*m* and a lateral inner cortical wall 251 are depicted to represent the bounds of the intramedullary canal 27 of the tibia 20. The fibula 60 is also shown for reference. FIG. 2B more clearly illustrates that as the eye moves from the proximal end 13 of the tibia 20 to the distal end of the tibia 20, the medial inner cortical wall 25*m* and the lateral inner cortical wall 251 taper as the metaphysis transitions into the diaphysis. In revision procedures in which a prior-installed tibial component is removed through undercutting the proximal tibia below the prior resected tibial surface, the total usable area of the intramedullary canal 27 decreases, particularly at the proximal end 13 (i.e., note how the metaphysis (i.e., the area of the generally wedge shaped portion) of the intramedullary canal 27 near the proximal end 13 would further decrease if the position of the resected tibial surface 23 were positioned any lower).

Figure 2C:
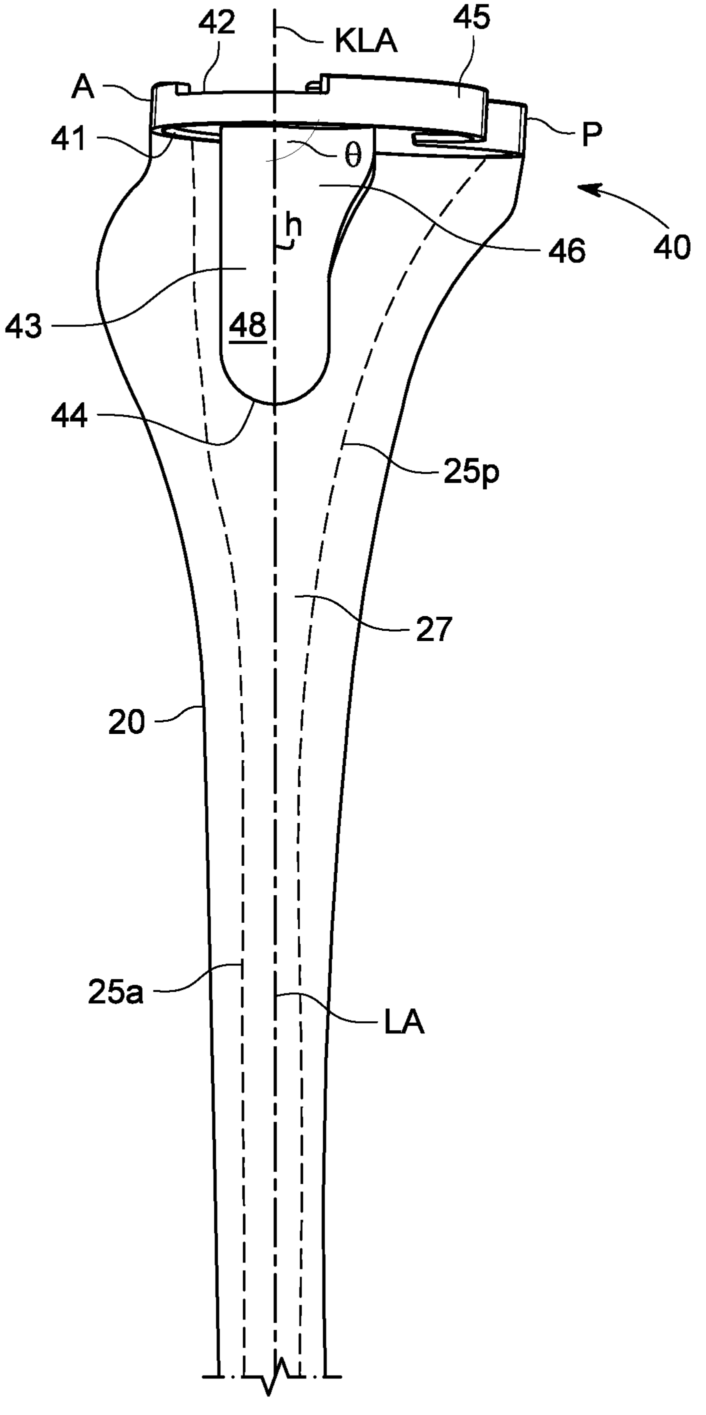
FIG. 2C is a side view of the exemplary tibial component of FIG. 2A shown implanted on and in a resected tibia. The resected tibia is shown in cross-section.

FIG. 2C provides a side view of the tibial component 40 of FIG. 2A implanted on the resected tibia 20. As can be seen in the side view of FIG. 2C, the baseplate 45 has a keel posterior angle θ that slopes downwardly from the anterior side A to the posterior side P of the knee. Furthermore, the keel longitudinal axis KLA of the tibial component 40 is shown essentially aligned with the longitudinal axis LA of the tibia 20 while being perpendicular to sagittal plane SP and the coronal plane CP when the tibial component 40 is in the installed configuration. The longitudinal axis of the tibia is also known as the anatomic axis of the tibia by those skilled in the art. "Anatomic axis of the tibia" is also sometimes used interchangeably with "mechanical axis of the tibia" because the anatomic axis of the tibia and the mechanical axis of the tibia are co-axial for most patients.

Without being bound by theory, it is contemplated that by having a sloped baseplate 45 relative to the keel longitudinal axis KLA in the manner described, that extends into the intramedullary canal 27 when the tibial component 40 is in the installed configuration such that the keel 43 is substantially aligned with (i.e., is coaxial with) the longitudinal axis LA of the tibia 20 and such that the keel 43 is disposed perpendicular to a sagittal plane SP (see FIG. 5) and a coronal plane CP (see FIG. 5), the exemplary tibial component 40 permits the keel 43 to extend generally downwardly into the intramedullary canal 27 of the tibia 20 without having the distal end 44 of the keel 43, or any other part of the keel 43 contact the inner cortical wall 25 of the tibia 20. In this manner, exemplary tibial components 40 substantially reduce the risk of the distal end 51 of the stem construct breaching the proximal cortical bone while orienting the baseplate 45 at a compound angle that can be used to more accurately reconstruct the patient's native, prediseased joint line. In FIG. 2C, a posterior inner cortical wall 25*p* and an anterior inner cortical wall 25*a* are depicted.

However, it will be appreciated that the exemplary tibial components 40, when in the installed configuration, do not necessarily need to have the keel longitudinal axis KLA to be fully aligned with the longitudinal axis LA of the tibia 20. In such embodiments, the keel 43 is not necessarily disposed perpendicular to both the sagittal plane SP and the coronal plane CP (see FIG. 5). Full alignment is considered desirable because it is thought to maximize available remaining space in the intramedullary canal 27, but partial alignment may be more appropriate in a given situation depending upon a number of factors, including patient anatomy, position of reactions, and surgeon preference. As such, disposing the keel longitudinal axis KLA at an angle relative to the longitudinal axis LA of the tibia 20 is considered to be within the scope of this disclosure.

As a result, and without being bound by theory, it is contemplated that the exemplary embodiments disclosed herein may permit the surgeon to insert longer keels 43 into the tibia 20 than was previously possible, especially in cases where the resected proximal end 13 of the tibia 20 was disposed at a slope (particularly at a compound angle comprising a varus tilt 90-δ and a posterior slope 90-θ). The longer keels 43 can more firmly stabilize and secure the tibial component 40 to the tibia 20 in kinematic alignment procedures and in anatomic alignment procedures over what was previously possible. It is still further contemplated that by aligning the keel longitudinal axis KLA with the longitudinal axis LA of the tibia 20, the force vectors that result from the natural ambulatory movement of the knee can be more stably transferred through the tibial component 40 to the tibia 20 and thereby prolong the useful life of the endoprosthetic knee implant 1. For example, when a person is standing, it is thought that the force exerted on the tibial component 40 from the mass of the person above the tibial component 40 can be more stably transferred to the feet of the person because the keel 43 of the tibial component 40 is desirably oriented closer to the mechanical axis of the tibia 20 (i.e., the longitudinal axis LA). The tibia has naturally evolved to distribute the force of the mass of a person generally along the mechanical axis toward the feet. By substantially aligning the keel longitudinal axis KLA with the longitudinal axis of the tibia, it is thought that the exemplary embodiments described herein may preserve the natural force distribution and kinematics of a pre-diseased natural knee over what was previously possible.

FIGS. 3A-4C show exemplary embodiments of a tibial component 40 of an endoprosthetic knee implant 1, wherein the distal end 44 of the keel 43 is configured to selectively attach to a distal stem extension 100. A surgeon may elect to use a distal stem extension 100 when there is a need to further stabilize the tibial component 40 in the intramedullary canal 27 of the tibia 20. FIG. 3A shows a side view of a right knee tibial component 40 having a keel varus angle δ (better visualized in FIG. 3C) and a keel posterior angle θ. The depicted tibial component 40 is similar to the exemplary embodiment shown in FIGS. 1A-2C. However, rather than having a rounded distal end 44, the depicted keel 43 is configured to selectively connect to a distal stem extension 100. It will be appreciated that the connecting elements on the distal end 44 of the keel 43 and the proximal end 49 of the stem extension 100 can be complementary mating elements. For example, the distal end 44 may have one or more projections and the proximal end 49 may have one or more complementary receivers designed to selectively and closely receive the one or more projections, or vice versa. In this manner, the keel 43 can be said to be "configured to selectively connect" or "configured to selectively attach" to a distal stem extension 100. Likewise, the distal stem extension 100 can be said to be "removably engaged" to the keel 43. In certain exemplary embodiments, the projections and complementary receivers desirably lockingly engage one another in an installed configuration. For example, certain exemplary embodiments can have a frustoconical or a frustopyramidal projection on either the distal end 44 of the keel 43 or the proximal end 49 of the stem extension 100. To continue the example, the receiver (i.e., the proximal end 49 of the stem extension 100 if the projection comprises the distal end 44 of the keel 43, and vice versa) can be a complementary frustoconical or frustopyramidal receiver designed to selectively and closely receive the projection of the mating element (e.g., either the distal end 44 of the keel 43 or the proximal end 49 of the stem extension 100). In other exemplary embodiments, the projections and complementary receivers can be screw threads. Combinations of the foregoing are considered to be within the scope of this disclosure.

In the depicted embodiment, the distal end 44 of the keel 43 comprises a tapered bore, the bore is sized to closely receive a tapered extension on the proximal end 49 of the distal stem extension 100, in a press-fit secured configuration. As can be seen in FIG. 3A, the keel 43 and the distal stem extension 100 together form a stem construct 143 having a substantially continuous keel longitudinal axis KLA.

Although FIGS. 3A-4C depict exemplary tibial components 40 comprising selectively attachable stem extensions 100, it will be appreciated that offset adaptors and angle adaptors can be configured to attach to the distal end 44 of the keel 43 in the same manner as the distal stem extension 100. Such offset adapters or angle adaptors can be used in lieu of or in addition to the distal stem extension 100. When both an adaptor and a stem extension are present, an offset adaptor, an angle adaptor, or a combination thereof would commonly be disposed between the distal end 44 of the keel 43 and the proximal end 49 of the distal stem extension 100. However, in exemplary embodiments comprising a modular keel 43 (see FIGS. 7A-8), the offset adaptor or angle adaptor, or a combination thereof, could be disposed between the proximal end 61 of the modular keel 43 and the lower end 41 of the baseplate 45.

As can be seen in the side view of FIG. 3A, the baseplate 45 is configured to slope downwardly from the anterior side A to the posterior side P of the tibial component 40 relative to the keel longitudinal axis KLA to define a keel posterior angle θ as described above. Stated differently, the intersection of the anterior-posterior line A-P line of the baseplate plane BPP with the transverse plane TRP at the posterior side P of the baseplate 45 defines a posterior slope 90-θ. The posterior slope 90-θ may be greater than zero degrees degree to less than or equal to fifteen degrees, preferably between 1 degree and ten degrees. However, in many applications, the posterior slope 90-θ is set at about three degrees.

The distal stem extension 100 may have grooves 98 disposed generally parallel to the keel longitudinal axis KLA when installed on the keel 43. These grooves 98 can facilitate the installation of the distal stem extension 100 into the intermedullary canal 27 (FIG. 4), especially when the distal stem extension 100 is a press fit stem extension. These grooves 98 can mitigate the displacement of medullary bone and marrow when the distal stem extension 100 is inserted into the tibial diaphysis. Displaced medullary bone and marrow can flow upwardly through these grooves 98 toward the still exposed tibial resected surface 23 to thereby be collected and disposed of. Without these grooves 98, the distal stem extension 100 could capture air in the intramedullary canal 27 or otherwise build up pressure and risk breaching the proximal cortex of the bone. The grooves 98 can also secure the distal stem extension 100 rotationally within intramedullary canal 27. When the distal stem extension 100 is a cemented distal stem extension such as the one depicted in FIG. 3A, the grooves 98 also provide additional space in which bone cement can be disposed between the distal stem extension 100 and the walls of the intramedullary canal 27.

The distal end 51 of the distal stem extension 100 can be selected from a variety of shapes. In certain exemplary embodiments, the distal end 51 of the distal stem extension 100 can be rounded, substantially straight, wedge shaped, wedge shaped with a rounded end, conical, conical with a rounded end, frustoconical, frustoconical with a rounded end, pyramidal, pyramidal with a rounded end, frustopyramidal, frustopyramidal with a rounded end, or combinations thereof. Shapes that have a generally convex profile are generally preferable to reduce the risk of unnecessarily ablating cancellous bone and bone marrow during the installation process. All such shapes having a generally convex profile and considered to be within the scope of this disclosure.

Without being bound by theory, it is contemplated that a removable distal stem extension 100 may permit surgeons to select from a group of available distal stem extensions 100 provided in a kit on the day of the procedure. Common of types of distal stem extensions 100 include press-fit stem extensions and cemented stem extensions. The surgeon or the technician can select from the provided group of available stem extensions 100 to effectively change the overall height of the tibial component 40 without having to rely on selectively testing and removing multiple unitary tibial components 40. The number of distal stem extensions 100 available to the surgeon can depend upon a number of factors, including the existence of a pre-operative measurements taken of the interior of the tibia 20 through radiography or other imaging methods.

Figure 3B:
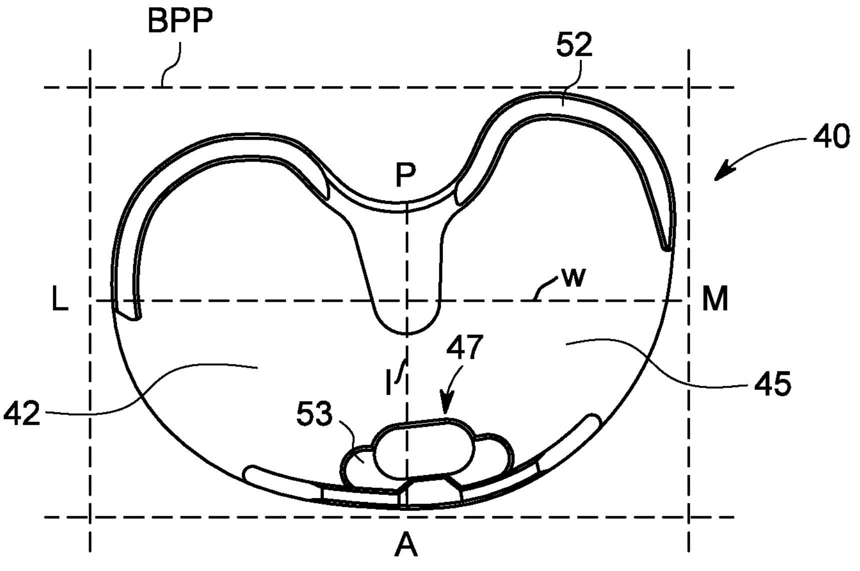
FIG. 3B is a top view of the exemplary tibial component of FIG. 3A.
Figure 3C:
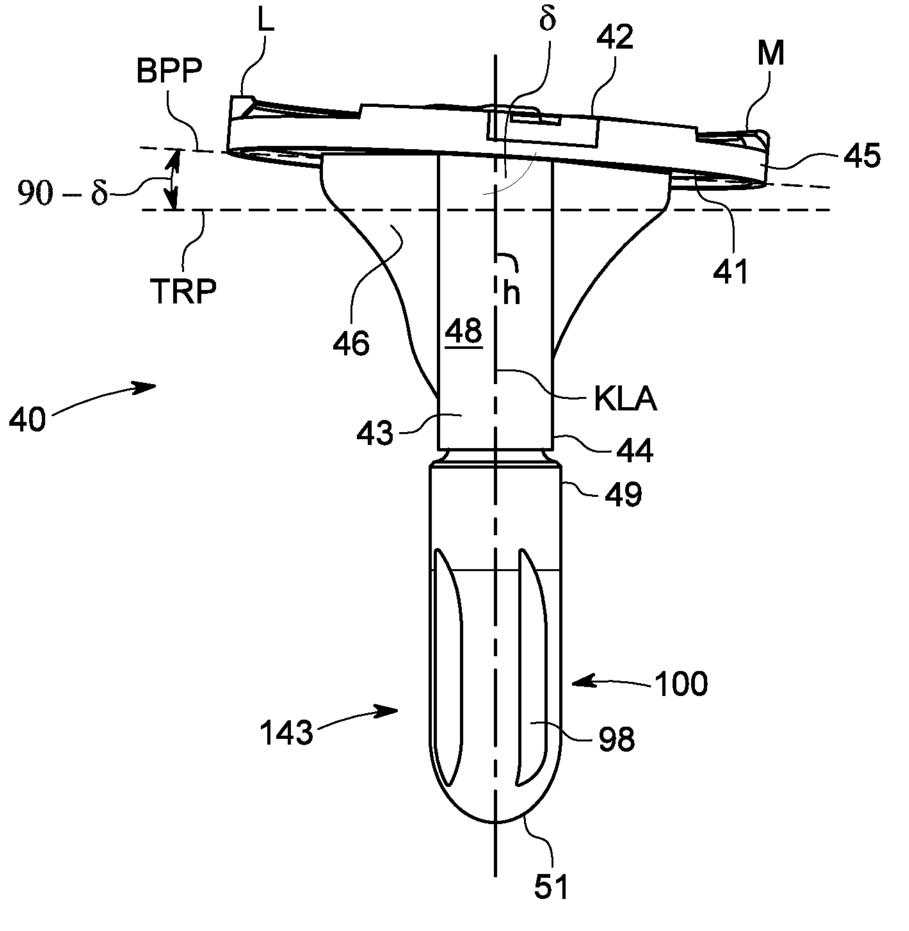
FIG. 3C is a front view of the exemplary tibial component of FIG. 3A.

FIG. 3B shows a top down view of the exemplary tibial component 40 of FIG. 3A. As can be seen in the frontal view or A-P view of the exemplary tibial component 40 in FIG. 3C, the baseplate 45 is configured to slope downward from the lateral side L to the medial side M of the tibial component 40 relative to the keel longitudinal axis KLA to thereby define the keel varus angle δ as described above. Stated differently, the medial-lateral line M-L of the baseplate plane BPP intersects the transverse plane TRP to define a varus tilt 90-δ. The varus tilt 90-δ can be in a range of greater than zero degrees to less than or equal to seven degrees. However, in many applications, the varus tilt 90-δ is set at about three degrees. It will be appreciated that tibial components 40 having different combinations of preset posterior slopes 90-θ and varus tilts 90-δ are considered to be within the scope of this disclosure.

Figure 4A:
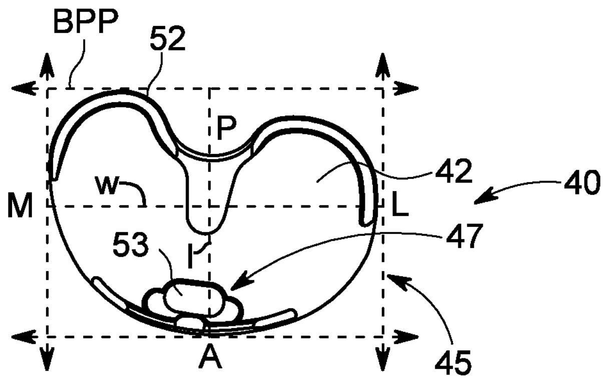
FIG. 4A is a top view of an exemplary embodiment of a tibial component of an endoprosthetic knee implant, featuring a left knee modular tibial component comprising a baseplate having a varus tilt and a posterior slope relative to a transverse plane.
Figure 4B:
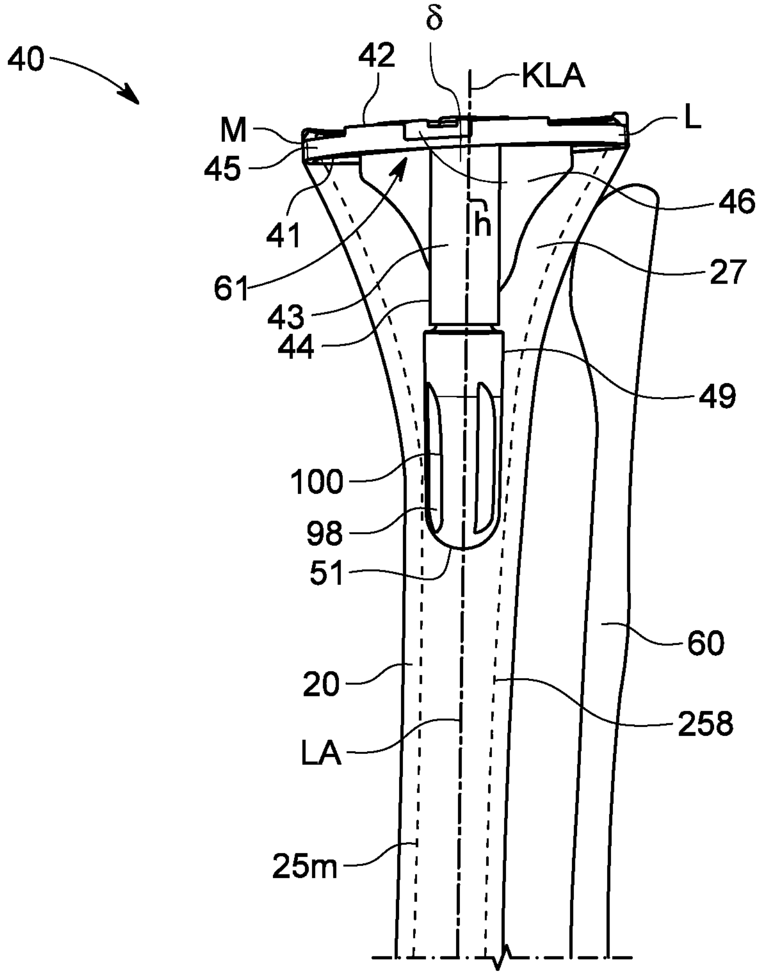
FIG. 4B is a front view of the exemplary tibial component of FIG. 4A shown implanted on and in a resected tibia. The resected tibia is shown in cross-section.

FIG. 4A is a top-down view of one embodiment of an exemplary tibial component 40 in accordance with this disclosure. FIG. 4B shows the tibial component 40 implanted on a resected proximal tibia 20. The tibial component 40 of FIG. 4A is configured for use on a left knee and is therefore substantially a mirror image of the tibial component 40 shown in FIGS. 3A-3C. As can be seen in the anterior view of FIG. 2B, the tibial baseplate 45 has a keel varus angle δ that slopes downwardly from the lateral side L to the medial side M of the knee.

Figure 4C:
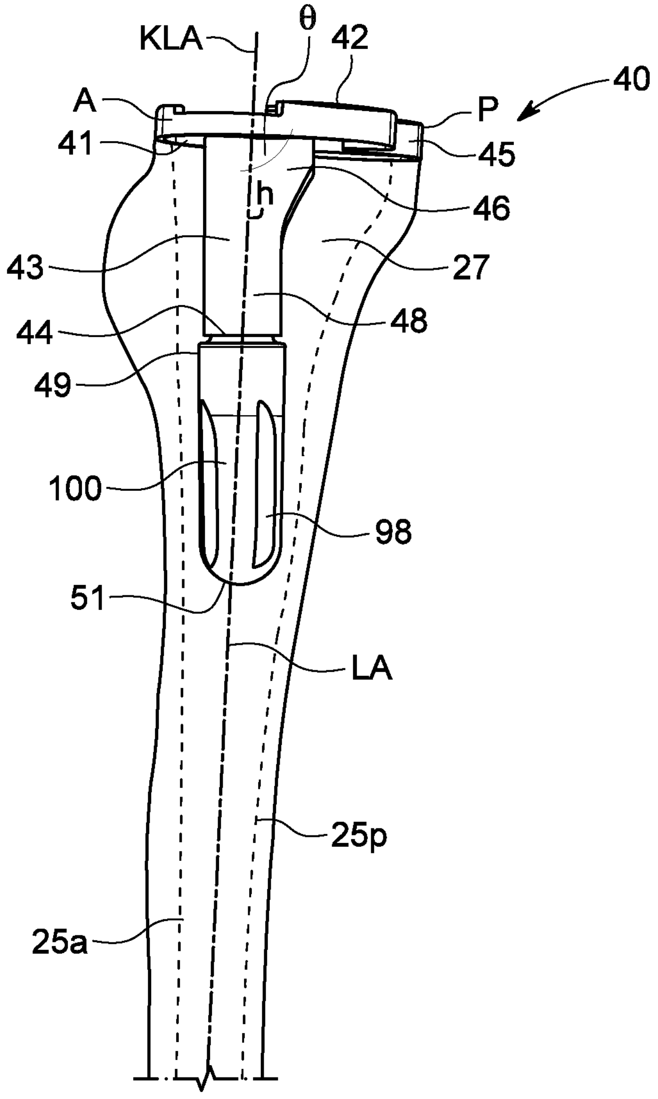
FIG. 4C is a side view of the exemplary tibial component of FIG. 4A shown implanted on a resected tibia. The resected tibia is shown in cross-section.

FIG. 4C provides a side view of the exemplary tibial component 40 of FIG. 4A implanted on the resected tibia 20. As can be seen in the side view of FIG. 4C, the tibial baseplate portion 45 has a keel posterior angle θ that slopes downwardly from the anterior side A to the posterior side P. In certain cases (e.g., revision cases), augments can be attached to the lower surface 41 of the baseplate 45 to compensate for poor or missing bone.

Without being bound by theory, it is contemplated that by having a sloped baseplate 45 relative to the keel longitudinal axis KLA in the manner described that extends into the intramedullary canal 27 when the tibial component 40 is in the installed configuration such that the stem construct 143 is substantially aligned with the longitudinal axis LA of the tibia 20 and such that the stem construct 143 is disposed perpendicular to a sagittal plane SP (see FIG. 5) and a coronal plane CP (see FIG. 5), the exemplary tibial component 40 permits the stem construct 143 to extend generally downwardly into the intramedullary canal 27 of the tibia 20 without having the distal end 51 of the stem construct 143, or any other part of the stem construct 143 contact the inner cortical wall 25 of the tibia 20. In this manner, exemplary tibial component 40 substantially reduces the risk of the distal end 51 of the stem construct breaching the proximal cortical bone while orienting the baseplate 45 at a compound angle that can be used to more accurately reconstruct the patient's native, pre-diseased joint line. In FIG. 4C, a posterior inner cortical wall 25*p* and an anterior inner cortical wall 25*a* are depicted for reference.

As a result, it is contemplated that the exemplary embodiments disclosed herein may permit the surgeon to insert longer stem constructs 143 into the tibia 20 than was previously possible in cases where the resected proximal end 13 of the tibia 20 was disposed at a slope (i.e., in a prior kinematic alignment or anatomic alignment procedure. Previously, stemmed revision-style tibial components were only usable with a revision mechanical alignment procedure regardless of whether the patient had undergone a primary kinematic alignment or a primary anatomic alignment procedure. Such procedures were previously not possible because of the amount of bone that had to be removed to extract the pre-existing implant and because the removal of existing bone necessarily reduced the amount of available volume (particularly the length and width dimensions) in the remaining intramedullary canal 27 in which to insert a stabilizing keel 43 or stem construct 143.

It is further contemplated that the exemplary embodiments described herein may permit a surgeon to perform a kinematic alignment or an anatomical alignment procedure in a revision procedure (i.e., a secondary surgery in which the original implant is removed) or in trauma cases that feature severely compromised tibial bone. Without being bound by theory, it is conceivable that a patient who underwent a mechanical alignment knee arthroplasty during a primary or prior revision procedure may now be able to benefit from a kinematic or anatomic alignment procedure.

Nothing in this disclosure limits the use of the exemplary tibial components and related instruments therefore to revision procedures, however. It is contemplated that such exemplary tibial components and/or exemplary instruments described herein can be used in primary procedures. It is believed that surgeons may especially benefit from the embodiments of the present disclosure in stemmed primary procedures.

Stemmed primary procedures are often used with patients with a high body mass index or that suffer from poor bone quality. It is thought that the use of a distal stem extension 100 in these cases can more reliably and more effectively distribute the stationary and ambulatory forces that a patient and the tibial component 40 with a stem construct 143 experiences.

In this manner, it is contemplated that the longer stem constructs 143 can more firmly stabilize and secure the tibial component 40 to the tibia 20 in kinematic alignment procedures and in anatomic alignment procedures over what was previously possible. It is still further contemplated that by aligning the keel longitudinal axis KLA with the longitudinal axis LA of the tibia 20, the force vectors that result from the natural ambulatory movement of the knee can be more stably transferred through the tibial component 40 to the tibia 20 and thereby prolong the useful life of the endoprosthetic knee implant 1.

As will be appreciated from the foregoing discussion, all embodiments of the tibial component 40 can be configured for use on right or left knees. In other exemplary embodiments, the exemplary tibial component can comprise a symmetric baseplate 45.

Referring to FIGS. 7A-7D, in certain exemplary embodiments the keel 43 is modular. That is, the keel 43 itself can selectively disengage the lower surface 41 of the baseplate 45 (see FIGS. 8A and 8B). The modular keel 43 can be produced in a number of different dimensions. It will be appreciated that the connecting elements on the lower surface 41 of the baseplate 45 and the proximal end 61 of the modular keel 43 can be complementary mating elements. For example, the lower surface 41 of the baseplate 45 may have one or more projections and the proximal end 61 of the modular keel 43 may have one or more complementary receivers designed to selectively and closely receive the one or more projections, or vice versa. In certain exemplary embodiments, the projections and complementary receivers desirably lockingly engage one another in an installed configuration. Combinations of the foregoing are considered to be within the scope of this disclosure. In this manner, the proximal end of the modular keel 43 is configured to engage the lower surface 41 of the baseplate 45.

It will be appreciated that the proximal end 61 of the modular keel can define a compound angle comprising a keel varus angle δ and a keel posterior angle θ. As a result, it is contemplated that the modular keel 43 can be chiral. That is, a left-sided modular keel 43 is configured to engage a left-sided baseplate 45 while a right-sided modular keel 43 is configured to engage a right-sided baseplate 45.

Figure 7C:
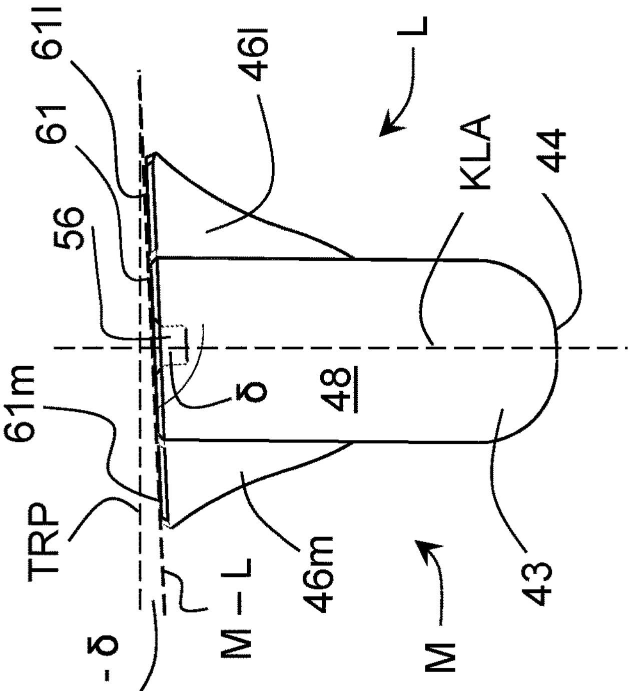
FIG. 7C is a front view of a modular keel for a left knee in an unassembled configuration.
Figure 7D:
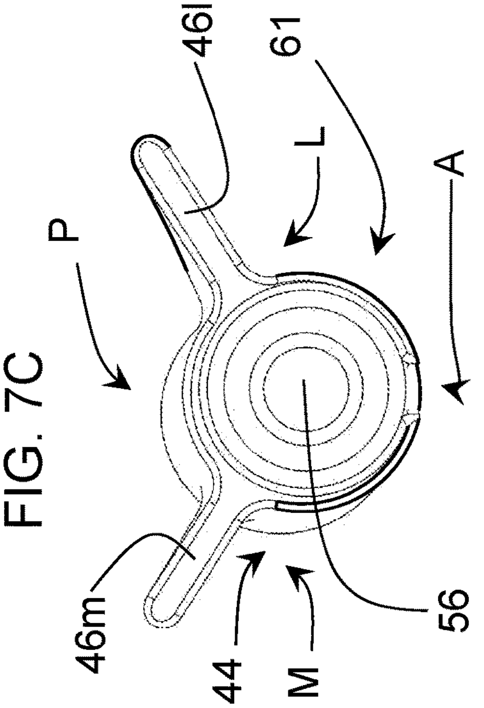
FIG. 7D is a top down view of the modular left-sided keel of FIG. 7C.
Figure 7A:
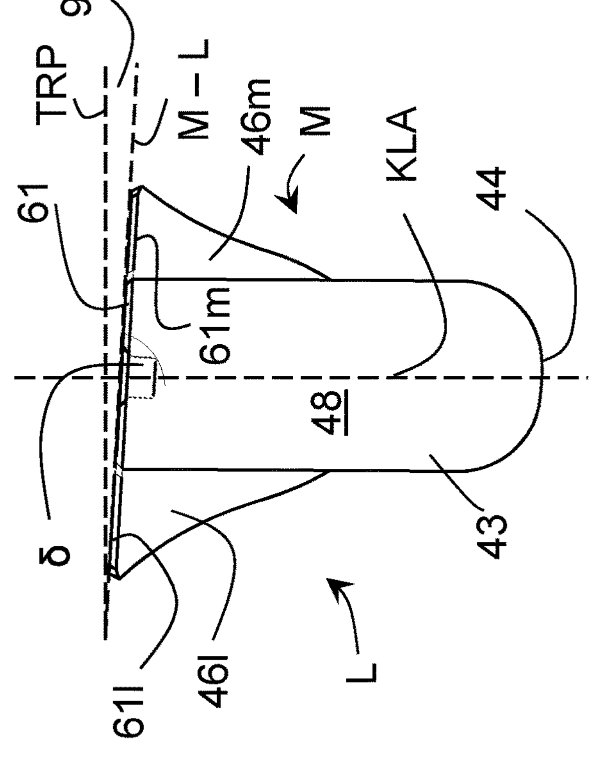
FIG. 7A is a front view of a modular keel for a right knee in an unassembled configuration.

FIG. 7A depicts a modular keel 43 for a right knee in an unassembled configuration. The depicted modular keel 43 comprises a body 48 and fins 46 extending transversely therefrom. A keel longitudinal axis KLA extends axially along the height h of the body 48 of the modular keel 43. The modular keel 43 comprises a proximal end 61 that is distally disposed from a distal end 44, a medial side M that is distally disposed from a lateral side L, and an anterior side A that is distally disposed from a posterior side P.

The modular keel 43 defines a compound angle at the proximal end 61, wherein the compound angle comprises a keel posterior angle θ (see FIG. 7E) and a keel varus angle δ. FIG. 7A is an anterior view of the exemplary modular keel 43 in which the modular keel 43 is oriented generally vertically (i.e., the keel longitudinal axis KLA extends generally up and down). The depicted orientation illustrates both the keel varus angle δ and the varus tilt 90-δ more clearly. Because the depicted embodiment is for a right knee and because the depicted modular keel 43 is oriented vertically in an anterior view, the proximal end 61*l* of the lateral fin 46*l* (depicted on the left side of the image in FIG. 7A) is disposed above the proximal end 61*m* of the medial fin 46*m* (depicted on the right side of the image in FIG. 7A). In this manner, the proximal end 61 of the keel 43 can be imagined to define medial-lateral line M-L. The keel varus angle δ can be visualized as the acute angle that results from the intersection of the medial-lateral line M-L with the keel longitudinal axis KLA, wherein the acute angle is disposed closer to the medial side M than the lateral side L.

When viewed in the depicted orientation, the proximal end 61 of the keel 43 can also be imagined to be disposed at a varus tilt 90-δ relative to a transverse plane TRP. It will be appreciated that when the depicted modular keel 43 is assembled with a modular baseplate 45 (see FIG. 8) (i.e., an assembled configuration), the medial-lateral line M-L of the proximal end 61 of the modular keel 43 is disposed parallel to the medial-lateral line M-L of the baseplate plane BPP.

As with the unitary embodiments, the varus tilt 90-δ of the modular keel 43 embodiments can be about three degrees for most patients, but angles greater than zero and less than or equal to seven degrees are considered to be within the scope of this disclosure. Multiple modular keels 43 may be provided at the time of a surgical procedure. Of the provided modular keels 43, one or more provided keels may have different compound angles (including but not limited to, for the sake of example, provided keels 43 having different keel varus angles δ, different keel posterior angles θ, or combinations thereof).

Figure 7B:
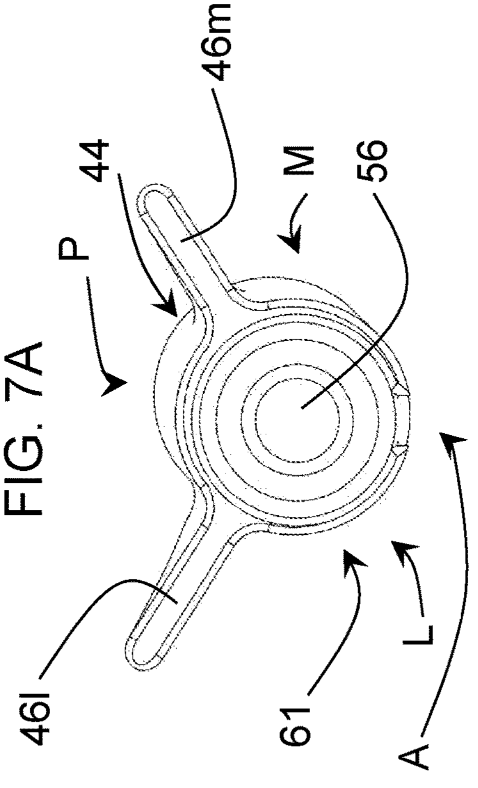
FIG. 7B is a top down view of the modular right-sided keel of FIG. 7A.

FIG. 7B is a top down view of the modular right-sided keel 43 of FIG. 7A. In FIG. 7B, the orientation of the keel 43 has been adjusted such that the proximal end 61 of the modular keel 43 is coplanar with the transverse plane TRP. In this orientation, the compound angle can be better visualized. The keel varus angle δ is visualized by the showing the distal end 44 of the modular keel 43 extending more toward the medial side M of the modular keel 43 than toward the lateral side L. The keel posterior angle θ is illustrated by showing the distal end 44 of the modular keel 43 also extending more toward the proximal side P of the modular keel 43 than the anterior side A. As shown more clearly with reference to FIG. 8, the proximal end 61 of the modular keel 43 can be selectively fixedly engaged (which can also be known as being "removably engaged") to a modular baseplate 45 in a number of ways appreciated by those having ordinary skill in the art, including all of the ways that a stem extension 100 can be selectively connected or attached to the distal end 44 of a keel 43. FIGS. 7A-7D depict a receiver 56 that can closely receive a projection 65 (FIGS. 8A-8B) extending from the lower surface 41 of a modular tibial baseplate 45 to thereby selectively fixedly engage the modular keel 43 to a modular tibial baseplate 45.

FIG. 7C depicts a modular keel 43 for a left knee in an unassembled configuration. The modular keel 43 of FIG. 7C is essentially a mirror image of the modular keel 43 depicted in FIG. 7A. Because the depicted embodiment is for a left knee and because the depicted modular keel 43 is oriented vertically in an anterior view, the proximal end 61*l* of the lateral fin 46*l* (depicted on the right side of FIG. 7C) is disposed above the proximal end 61*m* of the medial fin 46*m* (depicted on the left side of FIG. 7C). In this manner, the proximal end 61 of the keel 43 can be imagined to define medial-lateral line M-L. The keel varus angle δ can be visualized as the acute angle that results from the intersection of the medial-lateral line M-L with the keel longitudinal axis KLA, wherein the acute angle is disposed closer to the medial side M than the lateral side L.

When viewed in the depicted orientation, the proximal end 61 of the keel 43 can also be imagined to be disposed at a varus tilt 90-δ relative to a transverse plane TRP. It will be appreciated that when the depicted modular keel 43 is assembled with a modular baseplate 45 (FIG. 8) (i.e., an assembled configuration), the medial-lateral line M-L of the proximal end 61 of the modular keel 43 is disposed parallel to the medial-lateral line M-L of the baseplate plane BPP.

FIG. 7D is a top down view of the exemplary modular left-sided keel 43 of FIG. 7C. FIG. 7D is essentially a mirror image of the modular keel 43 depicted in FIG. 7B. In FIG. 7D, the orientation of the keel 43 has been adjusted such that the proximal end 61 of the modular keel 43 is coplanar with the transverse plane TRP. In this orientation, the compound angle can be better visualized. The keel varus angle δ is visualized by the showing the distal end 44 of the modular keel 43 extending more toward the medial side M of the modular keel 43 than toward the lateral side L. The keel posterior angle θ is illustrated by showing the distal end 44 of the modular keel 43 also extending more toward the proximal side P of the modular keel 43 than the anterior side A.

Figure 7F:
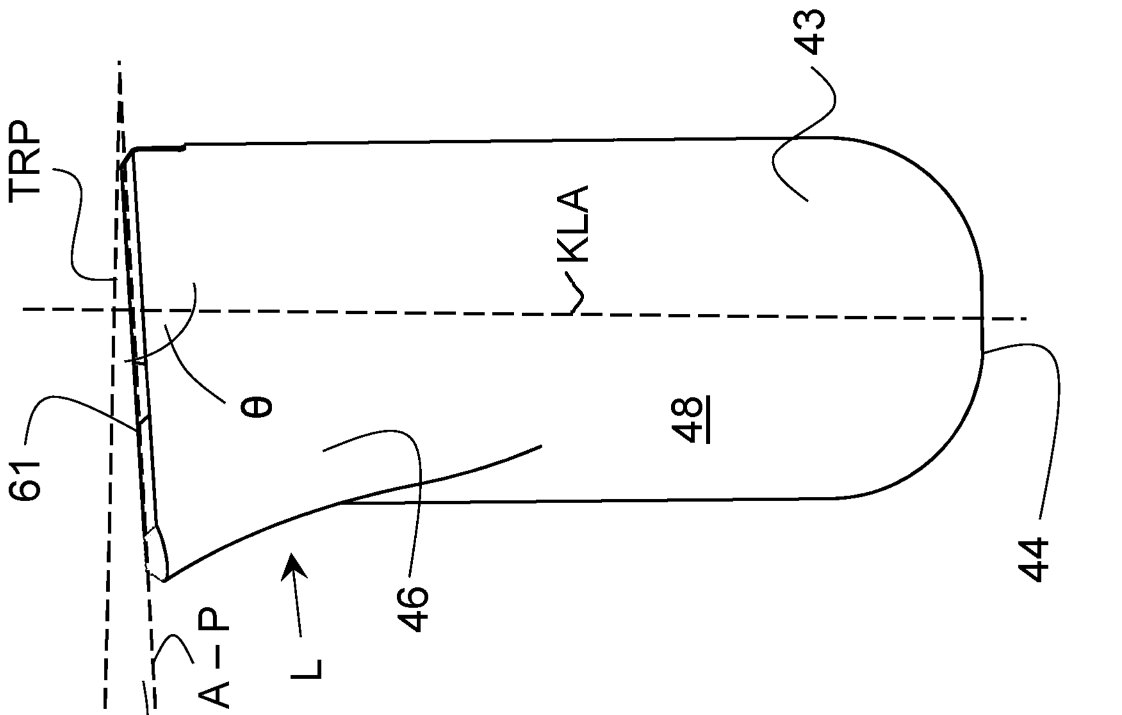
FIG. 7F is another side view of a modular keel in an unassembled configuration.
Figure 7E:
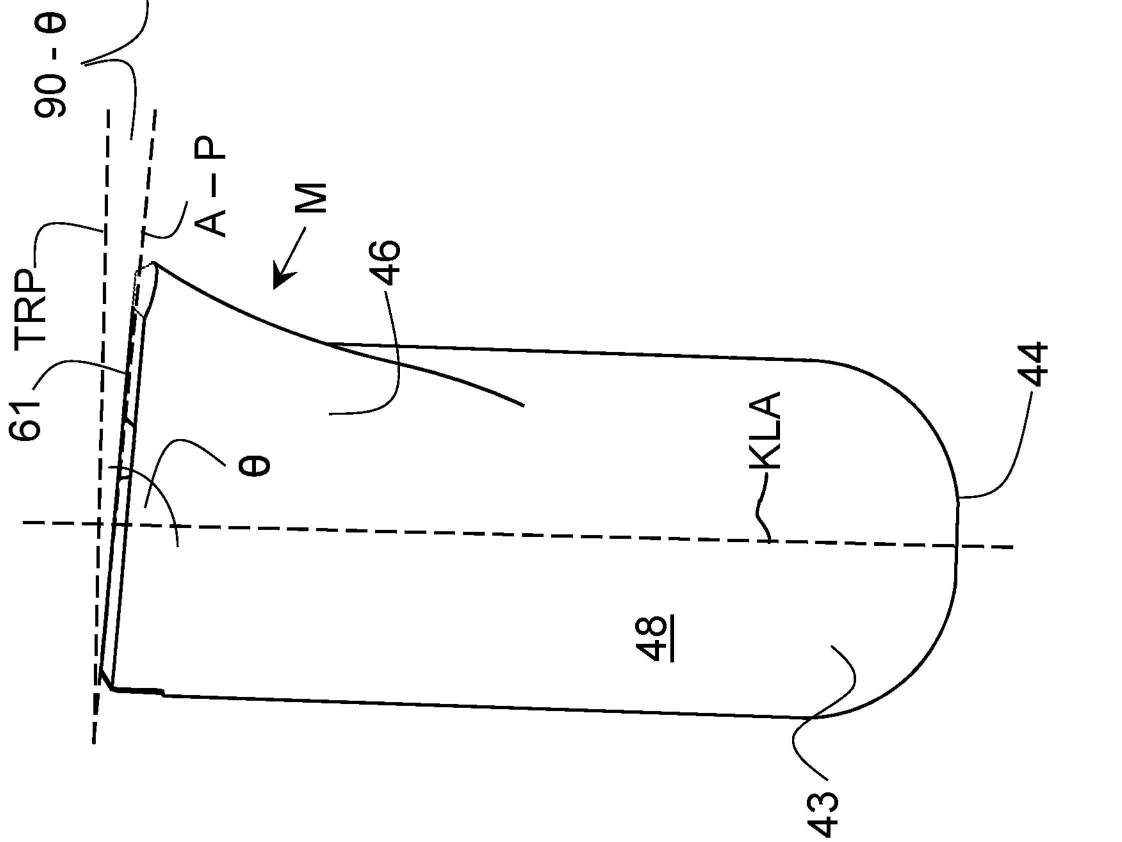
FIG. 7E is a side view of a modular keel in an unassembled configuration.

FIG. 7E is a medial side view of an exemplary modular keel 43 that is positioned to highlight the keel posterior angle θ. The keel posterior angle θ can be visualized as the acute angle that results from the intersection of the anterior-posterior line A-P with the keel longitudinal axis KLA, wherein the acute angle is disposed closer to the posterior side P than the anterior side A. When viewed in the depicted orientation, the proximal end 61 of the keel 43 can also be imagined to be disposed at a posterior slope 90-θ relative to a transverse plane TRP. It will be appreciated that when the depicted modular keel 43 is assembled with a modular baseplate 45 (see FIGS. 8A-8B) (i.e., an assembled configuration), the anterior-posterior line A-P of the proximal end 61 of the modular keel 43 is disposed parallel to the anterior-posterior line A-P of the baseplate plane BPP.

As with the unitary embodiments, the posterior slope 90-θ of the modular keel 43 embodiments can be about three degrees for most patients, but angles greater than zero and less than or equal to fifteen degrees are considered to be within the scope of this disclosure.

FIG. 7F is a lateral side view of an exemplary modular keel 43 wherein the proximal end is disposed at a compound angle relative to the keel longitudinal axis KLA, wherein the compound angle comprises a keel posterior angle θ and a keel varus angle δ. FIG. 7F is essentially a mirror image of the exemplary modular keel 43 depicted in FIG. 7E.

In certain exemplary embodiments, the modular keel 43 may have a distal end 44 that is not configured to engage a distal stem extension 100. In such embodiments, the distal end 44 of the modular keel 43 can be rounded, substantially straight, wedge shaped, wedge shaped with a rounded end, conical, conical with a rounded end, frustoconical, frustoconical with a rounded end, pyramidal, pyramidal with a rounded end, frustopyramidal, frustopyramidal with a rounded end, or combinations thereof. Shapes that have a generally convex profile are generally preferable to reduce the risk of unnecessarily ablating cancellous bone and bone marrow during the installation process. Such generally convex shapes can also reduce stress risers in the bone cement.

In other exemplary embodiments comprising a modular keel 43, the distal end 44 can be configured to selectively engage a distal stem extension 100 in substantially the same manner as described above (see generally FIG. 3A and FIG. 3C).

Without being bound to theory, it is contemplated that combinations of the modular keel 43 and of the distal stem extensions 100 can allow the surgeon to select a constructed tibial component 40 that more closely matches the patient's anatomy after the tibia 20 has been resected at a compound angle (comprising a posterior slope 90-θ and a varus tilt 90-δ) than what was previously available. The modular keel 43 and distal stem extension 100 may allow the surgeon to insert the stem construct 143 of an optimal height such that the keel longitudinal axis KLA is substantially aligned with the tibial longitudinal axis LA while being disposed generally perpendicular to an intersecting sagittal plane SP and a coronal plane CP. In this manner, surgeons can practice kinematic and anatomic alignment methods without risking using a shorter keel 43 or stem construct 100 on the tibial component 40 and without risking the keel 43 or stem construct 100 contacting an inner cortical wall 25*a*, 25*l*, 25*m*, 25*p* of the tibia 20.

Figure 8B:
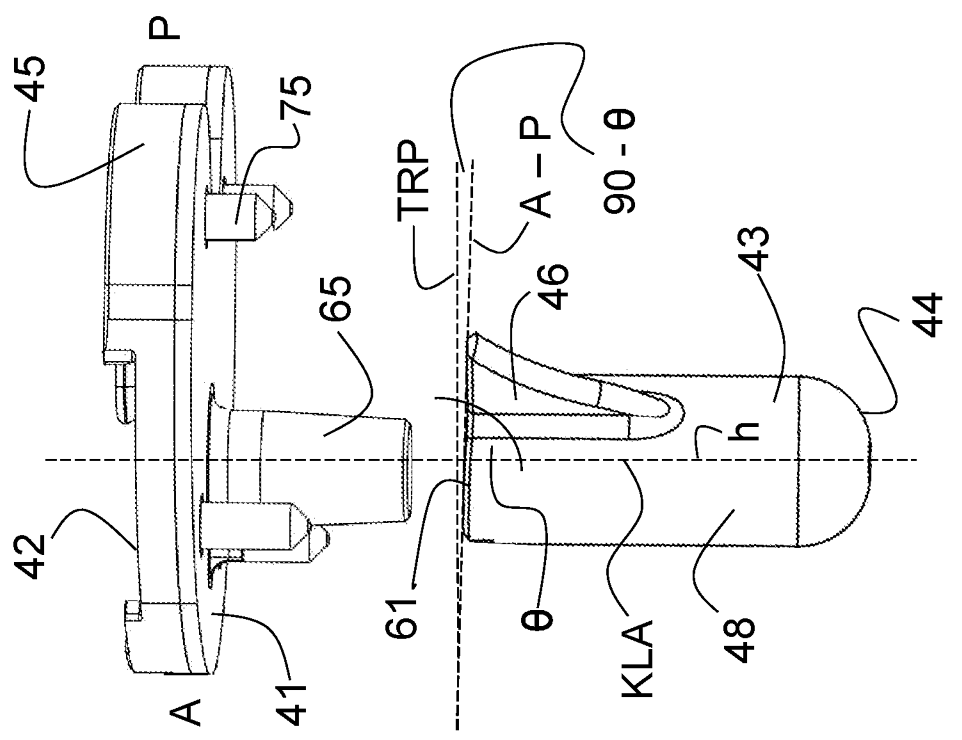
FIG. 8B is an expanded side view of an exemplary modular keel and modular baseplate.
Figure 8A:
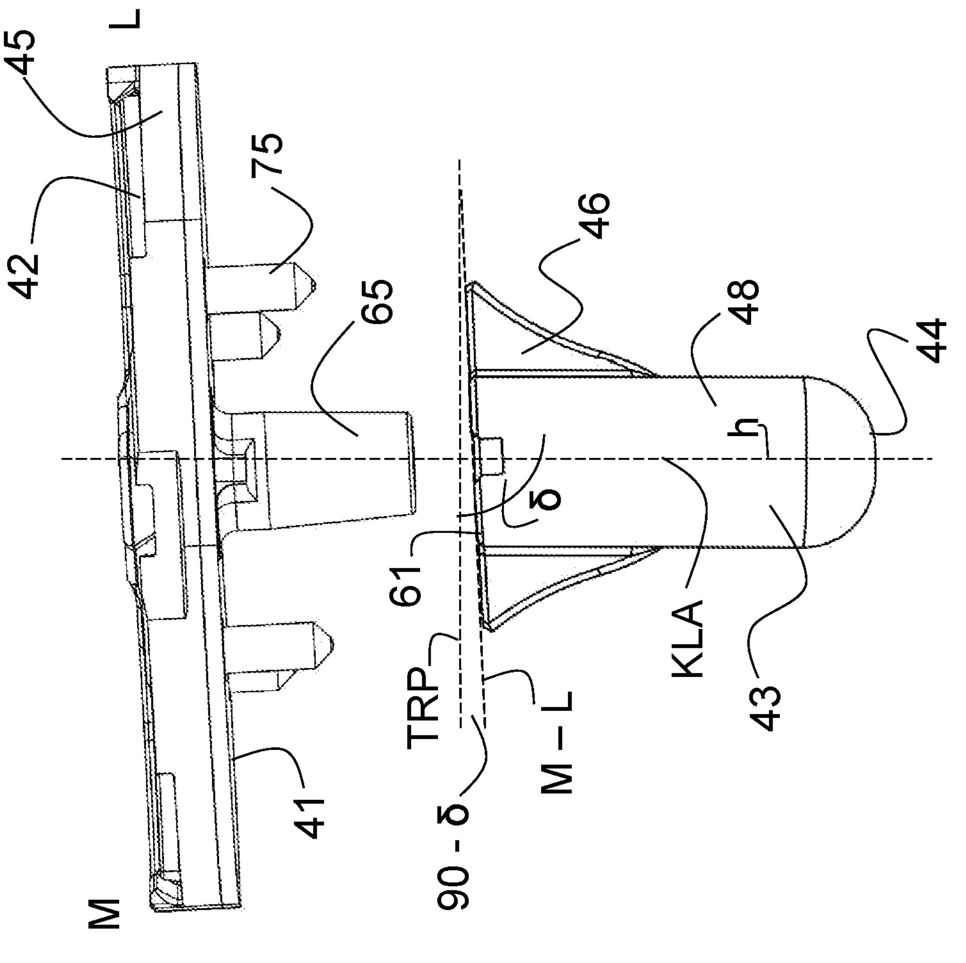
FIG. 8A is an expanded front view of an exemplary modular keel and modular baseplate.

FIG. 8A is a front view of an exemplary tibial component 40 comprising a modular keel 43 and a modular tibial baseplate 45 shown in an expanded view. It will be appreciated that when the modular keel 43 and the modular baseplate 45 do not engage one another, the modular keel 43 and/or the modular baseplate 45 can be said to be in an uninstalled and unassembled configuration. When the baseplate 45 fixedly engages the modular keel 43 (e.g., when the projection 65 descending from the lower surface 41 of the baseplate 45 is disposed in the receiver 56 at the proximal end 61 of the keel 43), the keel 43 and/or baseplate 45 can be said to in an assembled configuration. In this manner, the assembled keel 43 and baseplate 45 can be said to comprise an exemplary tibial component 40. When the assembled keel 43 and baseplate 45 are surgically implanted in a patient, the assembled keel 43 and baseplate 45 can be said to be in an installed configuration.

In the depicted embodiment, the projection 65 is a tapered projection and the receiver 56 is a tapered receiver that closely receives the tapered projection and, in this manner, "fixedly engages" the modular baseplate 45 to the modular keel 43. However, all methods of mechanically and securely engaging the modular keel 43 to the modular baseplate 45 are considered to be within the scope of this disclosure. Examples of such other mechanical engagement mechanisms include screws, pins, and any other locking projection and receiver mechanism known by those having ordinary skill in the art. FIG. 8A highlights the keel varus angle δ of the compound angle of the keel proximal end 61 and depicts the varus tilt 90-δ as described further above.

FIG. 8B is a side view of the exemplary tibial component 40 depicted in FIG. 8A. FIG. 8B highlights the keel posterior angle θ of the compound angle and depicts the posterior slope 90-θ as described further above.

Figure 11A:
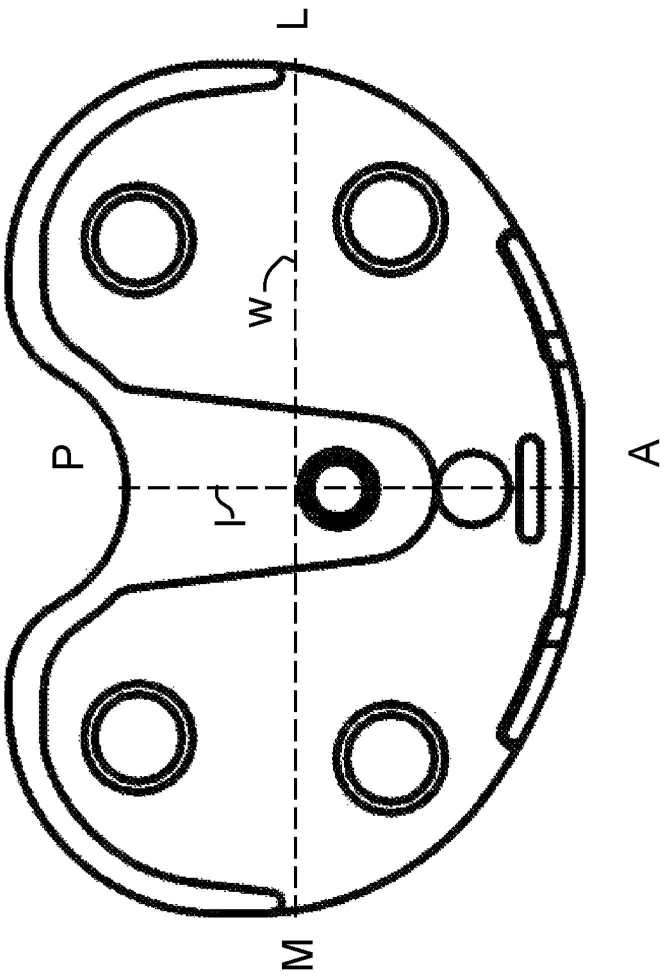
FIG. 11A is a top down view of an exemplary tibial component comprising a symmetric tibial baseplate.

FIG. 11A is a top down view of an exemplary tibial component 40 wherein the baseplate 45 is symmetric around the A-P bisecting line. As a subcomponent in an unassembled configuration, the depicted baseplate 45 can be used in either the right or left knee.

Figure 11C:
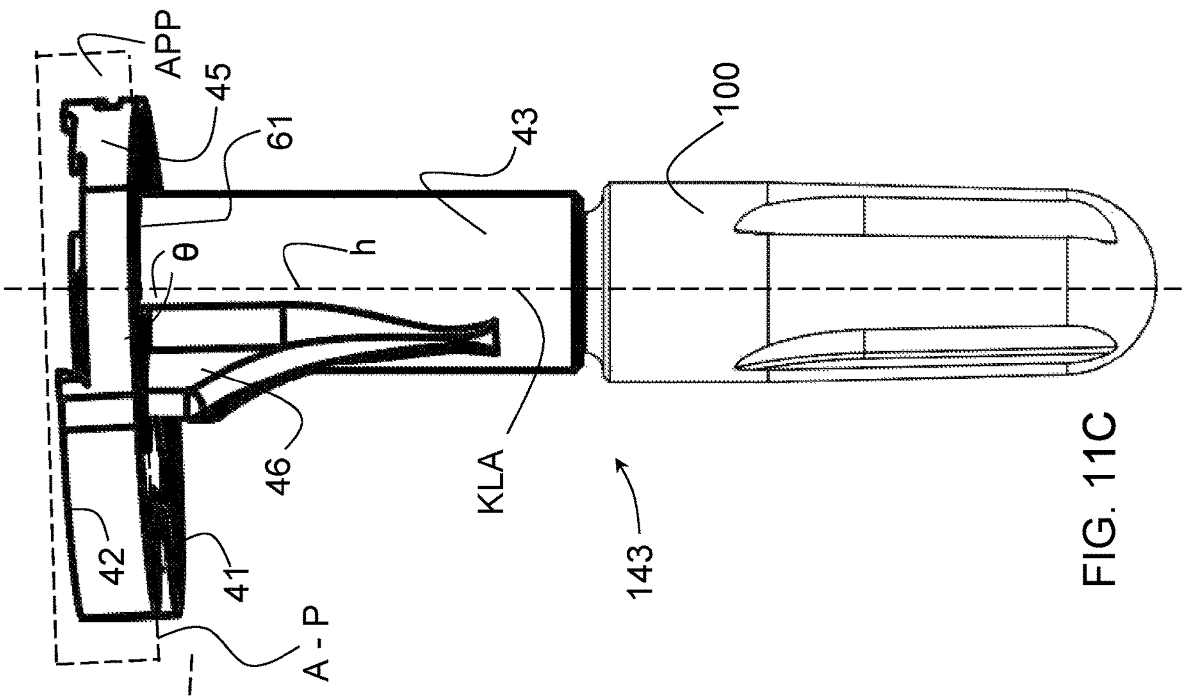
FIG. 11C is a medial side view of the exemplary tibial component of FIG. 11B.
Figure 11B:
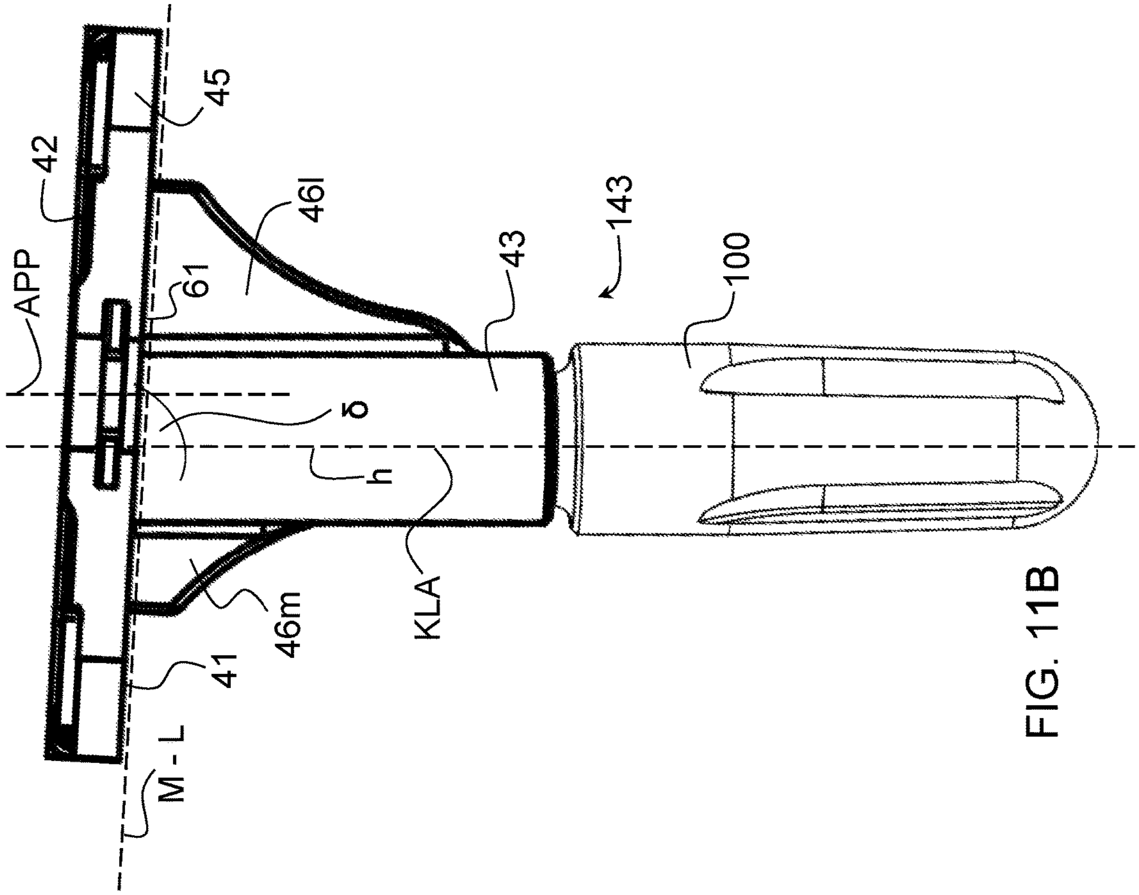
FIG. 11B is an anterior view of an exemplary tibial component wherein the keel longitudinal axis is offset from an anterior-posterior plane that bisects the tibial baseplate of FIG. 11A.

FIG. 11B is a front view of an exemplary tibial component 40 wherein the keel 43 is offset from a central anterior-posterior plane APP (see also FIG. 11C) that extends along the A-P line depicted in FIG. 11A. In the depicted embodiment and orientation, the central anterior-posterior plane APP bisects the baseplate 45 vertically along the A-P line to define the anterior-posterior plane APP and the keel longitudinal axis KLA is offset from the anterior-posterior plane APP medially. In other exemplary embodiments, the keel longitudinal axis KLA can be offset from the anterior-posterior plane APP laterally. In still other exemplary embodiments, it is contemplated that the keel longitudinal axis KLA can be offset from a medial-lateral plane anteriorly or posteriorly. Combinations of anterior, posterior, medial, and lateral offsets are considered to be within the scope of this disclosure. It is contemplated that most offsets would be less than 10 mm because the available space in most resected tibias 20 is limited.

The embodiment of FIG. 11B illustrates that the general placement of the fins 46 does not necessarily have to change to accommodate the offset keel 43. The medial fin 46*m* is smaller than the lateral fin 46*l* to accommodate the further reduced space in the medial side of the tibia. The space is further reduced due in part to the presence of the offset keel 43. As in the before discussed exemplary embodiments, the proximal surface 61 of the keel 43 is disposed at a compound angle relative to the keel longitudinal axis KLA wherein the compound angle comprises a keel posterior angle θ (FIG. 11C) and a keel varus angle δ.

The depicted embodiment shows the distal end of the keel 43 engaging a distal stem extension 100 to define a stem construct 143. However, in other exemplary embodiments, the distal end of the offset keel 43 can be generally rounded as described above. In other exemplary embodiments, the offset keel 43 can be modular and selectively attachable to the tibial baseplate 45. It is contemplated that modular offset keels 43 and unitary offset tibial components 40 can be provided in left knee and right knee configurations.

The tibial components 40 described herein can be provided in the form of a kit. For example, any of the tibial components 40, modular tibial baseplate 45, distal stem extensions 100, and modular keels 43 (including but not limited to non-offset modular keels and offset modular keels) can be provided with a plurality of different sizes. Chiral components can be provided for a left knee and a right knee. The tibial components 40 and/or the modular keels 43 can be provided in a number of different compound angles, wherein of the number of different compound angles, the compound angles differ by at least one of a difference in keel posterior angle θ and/or keel varus angle δ. Optionally, exemplary kits may further comprise offset adaptors, angle adaptors, augments, meniscal inserts, femoral components, trial components, or combinations of any thereof. The components of the kit are preferably arranged in a convenient format, such as in a surgical tray or case. However, the kit components do not have to be packaged or delivered together, provided that they are assembled or collected together in the operating room for use at the time of surgery.

An exemplary kit can include any suitable embodiment of an exemplary tibial component 40, variations of the exemplary tibial components 40 described herein, and any other exemplary tibial component 40 according to an embodiment (including sub-components thereof such as a modular keel 43 and a modular baseplate 45). While it is contemplated that an exemplary kit may include one or more tibial components 40 and one or more distal stem extensions 100, it will be appreciated that certain kits may lack some or all of these components.

Any suitable embodiment of a tibial baseplate 45, variations of the tibial baseplates 45 described herein, and any other tibial baseplate 45 according to an embodiment are considered to be within the scope of this disclosure.

Likewise, any suitable embodiment of a modular keel 43, variations of the modular keels 43 described herein, and any other modular keel 43 according to an embodiment are considered to be within the scope of this disclosure.

Still further likewise, any suitable embodiment of a distal stem extension 100, variations of the distal stem extensions 100 described herein, and any other distal stem extension 100 according to an embodiment are considered to be within the scope of this disclosure.

Selection of a suitable number or type of tibial components 40, tibial baseplates 45, modular keels 43, and distal stem extensions 100 to include in a kit according to a particular embodiment can be based on various considerations, such as the procedure intended to be performed using the components included in the kit.

Figure 9:
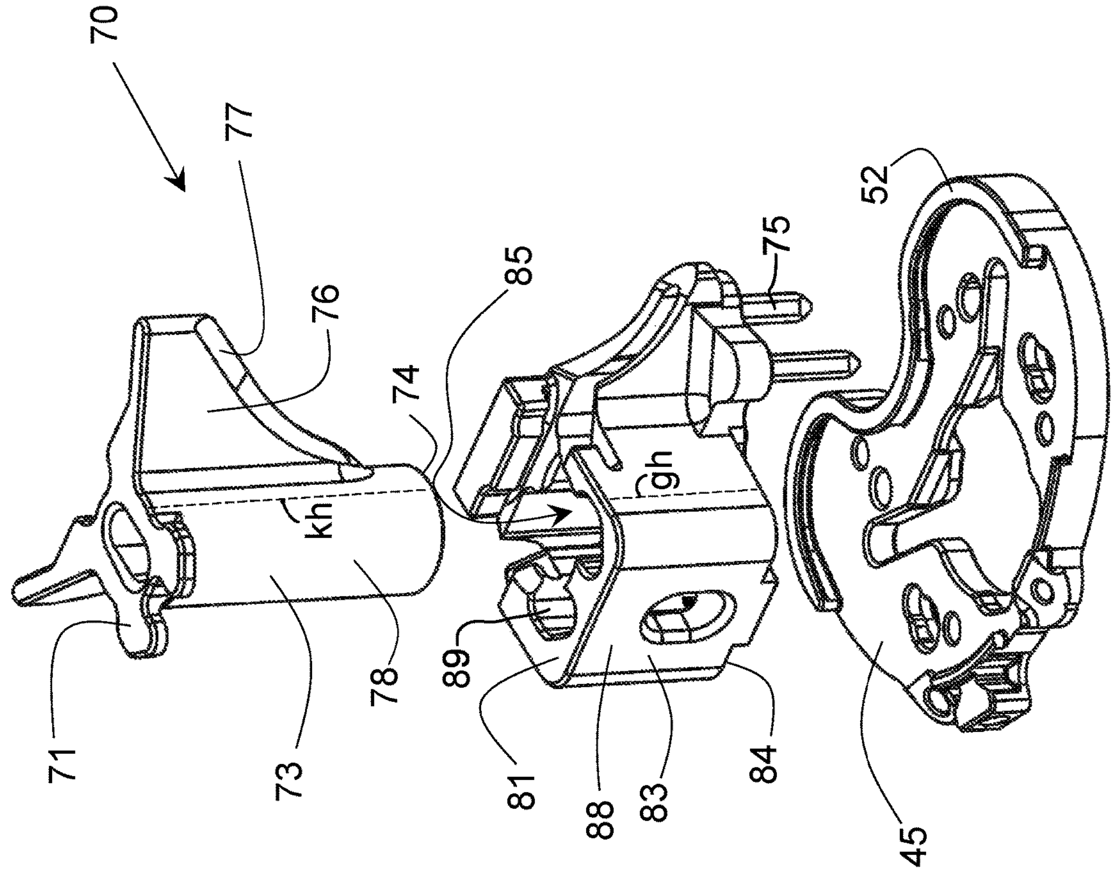
FIG. 9 is an expanded top down perspective view of an exemplary keel punch and punch guide disposed above a trial baseplate (i.e., in a non-assembled configuration).

FIG. 9 is a perspective view of an exemplary instrument assembly 70 depicted in an expanded (e.g., unassembled configuration). The components of the exemplary assembly comprise a keel punch 73 and a punch guide 83. The depicted punch guide 83 can also serve as a reamer guide. The keel punch 73 has a punch proximal end 71 distally disposed from a punch distal end 74 along a punch body 78. The punch proximal end 71 is disposed at a keel posterior angle θ relative to a keel longitudinal axis KLA extending along a height dimension kh of the keel punch 73. The punch proximal end 71 is disposed at a keel varus angle δ relative to the keel longitudinal axis KLA extending along the height dimension kh of the keel punch 73. The punch distal end 74 comprises a sharp edge. Punch fins 76 extend transversely from the punch body 78. The distal edges 77 of the punch fins 76 are desirably sharpened. The sharp edge of the punch distal end 74 and the sharp distal edges 77 of the punch fins 76 facilitate the displacement of intramedullary bone and marrow when inserted into the resected surface 23 of the tibia 20.

The punch guide 83 has a guide distal end 84 distally disposed from a guide proximal end 81 along a guide body 88. As seen more clearly in FIGS. 10A-10C, an inner wall 89 of the guide body 88 defines a through channel 85 that extends through the guide body 88 from the guide proximal end 81 to the guide distal end 84. The through channel 85 is complementary to the perimeter profile of the keel punch 73 and slightly larger than the perimeter profile of the keel punch 73. In this manner, the punch guide 83 can be said to be "configured to closely receive" the keel punch 73. Protrusions can extend from the guide distal end 84 to secure the punch guide 83 to the resected tibial surface 23 when in use.

Figures 10A, 10B, 10C, 10D:
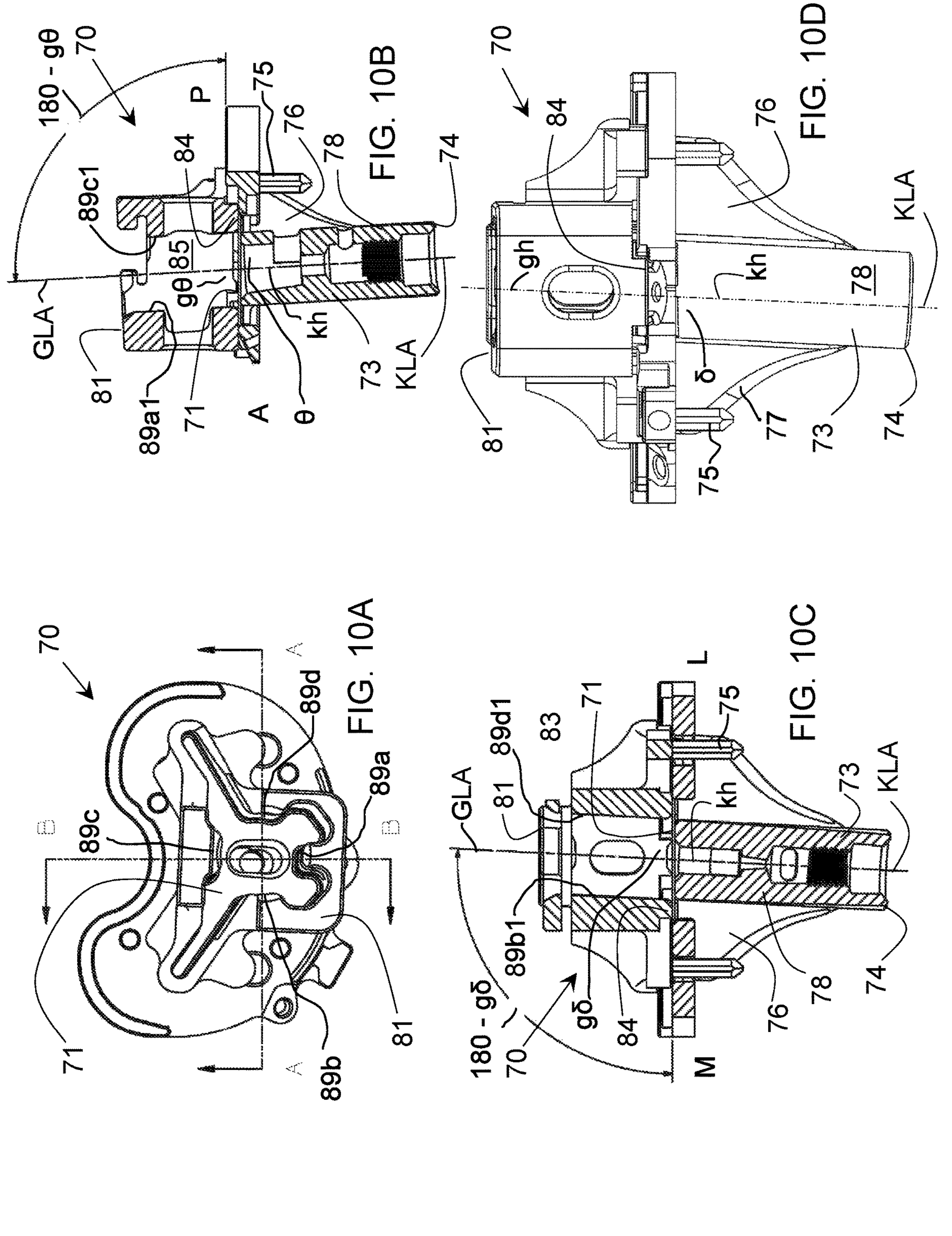
FIG. 10A is a top down view of the exemplary assembly of FIG. 10D.
FIG. 10B is a cross sectional view of the assembly of FIG. 10A taken along line B-B.
FIG. 10C is a cross sectional view of the assembly of FIG. 10A taken along line A-A.
FIG. 10D is an anterior view of an exemplary assembly (i.e., the components of FIG. 9 in an assembled configuration) comprising a keel punch and a punch guide engaging a trial baseplate.

The center portion of the through channel 85 of the depicted punch guide is further sized and dimensioned to guide a reamer into the tibial intramedullary canal 27. As seen in FIG. 10A, the inner wall 89 of the guide body 88 can comprise an anterior projection 89*a* that is distally disposed from a posterior projection 89*c* and a medial projection 89*b* that is distally disposed from a lateral projection 89*d*. The most projected surface of the projections 89*a*, 89*b*, 89*c*, 89*d* can desirably be concavely curved to accommodate the generally cylindrical profile of the reamer.

In practice, when the exemplary instruments are arranged in an assembled and installed configuration (discussed further below), the surgeon can first insert a reamer (which generally resembles a large threaded drill bit) through the through channel 85 to create an initial intramedullary cavity. Depending upon the size of the patient's tibia, multiple reamers of progressively larger sizes may be inserted through the through channel 85 to iteratively enlarge the dimensions of the initial intramedullary cavity. After the initial intramedullary canal has been reamed to the desired dimensions, the surgeon can remove the reamer and then insert an exemplary keel punch 73 through the through channel 85 to define an intramedullary cavity that is generally complementary to the profile of the keel punch 73. In certain exemplary procedures, multiple keel punches 73 of progressively larger sizes may be inserted through one or more punch guides 83 to define an intramedullary cavity that is generally complementary to the profile of the desired size of an exemplary keel 43 of an exemplary tibial component 40. It is contemplated that multiple exemplary punch guides 83 may be provided in different sizes at the time of the surgical procedure.

Referring back to the structure of the depicted exemplary punch guide 83 with particular reference to FIG. 10B, the guide distal end 84 is disposed at a guide posterior angle gθ relative to a guide longitudinal axis GLA (FIG. 10D) extending along a height dimension gh of the punch guide 83. In like manner, an anterior side 89*a*1 of the inner surface 89 and a posterior side 89*c*1 of the inner surface 89 are desirably disposed at the same guide posterior angle gθ as the distal guide end 84 relative to the guide longitudinal axis GLA such that the through channel 85 of the punch guide 83 slopes anteriorly to posteriorly from the guide proximal end 81 to the guide distal end 84. However, it will be appreciated that in other exemplary embodiments, the guide posterior angle gθ of the anterior side 89*a*1 and the posterior side 89*c*1 of the inner surface 89 can be different from the guide posterior angle gθ of the guide distal end 84. The guide posterior supplemental angle 180-gθ is also shown.

Moreover, as better seen in FIG. 10C, the guide distal end 84 is disposed at a guide varus angle gδ relative to the guide longitudinal axis GLA extending along the height dimension gh of the punch guide 83. In like manner, a medial side 89*b*1 of the inner surface 89 and a lateral side 89*d*1 of the inner surface 89 are desirably disposed at the same guide varus angle gδ as the distal guide end 84 relative to the guide longitudinal axis GLA such that the through channel 85 of the punch guide 83 slopes laterally to medially from the guide proximal end 81 to the guide distal end 84. However, it will be appreciated that in other exemplary embodiments, the guide varus angle gδ of the medial side 89*b*1 and the lateral side 89*d*1 of the inner surface 89 can be different from the guide varus angle gδ of the guide distal end 84. The guide varus supplemental angle 180-gδ is also shown.

FIG. 10D depicts an exemplary instrument assembly 70 in an assembled configuration. In operation, a surgeon may first place a trial tibial baseplate 45 to the resected surface 23 of the tibia 20. Once positioned, the surgeon can insert the protrusions 75 (e.g., spikes) of the punch guide 83 through receiving holes in the trial baseplate 45. The surgeon may use a mallet to hammer the protrusions 75 of the punch guide 83 through the receiving holes and into the resected tibia 20 to thereby secure the trial baseplate 45 and the punch guide 83 to the resected surface 23 of the tibia 20.

The keel punch 73 can be affixed to the distal end of a broach handle. The surgeon can insert the keel punch 73 through the through channel 85, which guides the keel punch 73 into the resected surface 23 of the tibia 20 at the desired keel posterior angle θ and keel varus angle δ. The surgeon may use a mallet to hammer the proximal end of the broach handle to insert the keel punch 73 into the resected surface 23 of the tibia 20. In this manner, the surgeon can create a keel cavity in the intramedullary canal 27 of the tibia 20 at the desired keel posterior angle θ and keel varus angle δ to accommodate an exemplary keel 43 of an exemplary tibia component 40.

It will be appreciated that the keel punch 73 and the punch guide 83 can be provided in different sizes. A surgeon may insert and remove successively larger sizes of the punch guide 83 and keel punch 73 to iteratively create a successively larger keel cavity in the intramedullary canal 27 until the desired size of the keel 43 of the tibial component 40 is achieved. Upon achieving the desired size and optionally evacuating any residual material from the keel cavity, the surgeon may insert the keel 43 of any of the exemplary tibial components 40 described herein into the keel cavity at the desired angle and position.

The exemplary instrument assemblies 70 described herein can be provided in the form of a kit. For example, the exemplary keel punch 73 and exemplary punch guide 83 can be provided with a plurality of different sizes. Chiral components can be provided for a left knee and a right knee. The keel punch 73 and/or punch guide 83 can be provided in a number of different compound angles, wherein of the number of different compound angles, the compound angles differ by at least one of a difference in keel posterior angle θ and/or keel varus angle δ. Optionally, exemplary kits may further comprise mallets, trial tibial baseplates, broach handles, or combinations of any thereof. The components of the kit are preferably arranged in a convenient format, such as in a surgical tray or case. However, the kit components do not have to be packaged or delivered together, provided that they are assembled or collected together in the operating room for use at the time of surgery.

An exemplary kit can include any suitable embodiment of an exemplary keel punch 73, variations of the exemplary keel punches 73 described herein, and any other exemplary keel punch 73 according to an embodiment. While it is contemplated that an exemplary kit may further include one or more trial tibial baseplates 45, it will be appreciated that certain kits may lack some or all of these components.

Any suitable embodiment of a punch guide 83, variations of the punch guides 83 described herein, and any other punch guide 83 according to an embodiment are considered to be within the scope of this disclosure.

Selection of a suitable number or type of keel punches 73 and punch guides 83 to include in a kit according to a particular embodiment can be based on various considerations, such as the procedure intended to be performed using the components included in the kit.

An exemplary tibial component of an endoprosthetic knee implant comprises: a tibial baseplate; and a keel extending from a lower surface of the tibial baseplate, wherein a keel longitudinal axis extends axially through the keel, wherein the tibial baseplate is disposed at a keel posterior angle relative to the keel longitudinal axis, and wherein the tibial baseplate is disposed at a keel varus angle relative to the keel longitudinal axis.

In an exemplary tibial component, the keel posterior angle can be less than 90 degrees and can be greater than or equal to about 75 degrees.

In an exemplary tibial component, the keel varus angle can be less than 90 degrees and can greater than or equal to about 83 degrees.

In an exemplary tibial component, a distal stem extension can be removably engaged to the keel.

In an exemplary tibial component, the keel can be a modular keel, and wherein the modular keel is removably engaged to the tibial baseplate.

In an exemplary tibial component, the keel longitudinal axis can be aligned with the longitudinal axis of the tibia in both the sagittal plane and the coronal plane when the tibial component is disposed in an installed configuration.

An exemplary tibial component comprises: a tibial baseplate having an upper surface, a lower surface, an anterior side distally disposed from a posterior side, and a medial side distally disposed from a lateral side, wherein a first line connecting the anterior side and the posterior side, defines an anterior-posterior line, wherein a second line connecting the medial side to the lateral side defines a medial-lateral line, and wherein the anterior-posterior line is disposed perpendicular to the medial-lateral line on a tibial baseplate plane; and a keel descending from the lower surface of the tibial baseplate, wherein the anterior-posterior line of the tibial baseplate is disposed at a posterior slope relative to a transverse plane intersecting the tibial component, and wherein the medial-lateral line of the tibial baseplate is disposed at a varus tilt relative to the transverse plane intersecting the tibial component.

In an exemplary tibial component, the posterior slope can be greater than zero degrees and can be less than or equal to about 15 degrees.

In an exemplary tibial component, the varus tilt can be greater than zero degrees and can be greater than or equal to about 7 degrees.

In an exemplary tibial component, a keel longitudinal axis can extend along a height of the keel, the keel longitudinal axis can be aligned with the longitudinal axis of the tibia when the tibial component is in an installed configuration.

In an exemplary tibial component, the tibial baseplate plane can be parallel to the anterior-posterior line and the medial-lateral line.

An exemplary modular keel comprises: a keel body; and a keel proximal end, wherein a keel longitudinal axis extends axially through the keel body, wherein the keel proximal end is disposed at a keel posterior angle relative to the keel longitudinal axis, and wherein the keel proximal end is disposed at a keel varus angle relative to the keel longitudinal axis.

An exemplary modular keel can further comprise fins extending transversely from the keel body.

An exemplary modular keel can further comprise a receiver in the keel proximal end, wherein the receiver is configured to selectively fixedly engage a complementary projection extending from a lower end of a tibial baseplate.

An exemplary modular keel can further comprise a projection in the keel proximal end, wherein the projection is configured to selectively engage a complementary receiver defined by a tibial baseplate.

An exemplary instrument assembly can comprise: a keel punch, the keel punch having a punch proximal end distally disposed from a punch distal end along a body, wherein the punch proximal end is disposed at a keel posterior angle relative to a keel longitudinal axis extending along a height dimension of the keel punch, and wherein the punch proximal end is disposed at a keel varus angle relative to the keel longitudinal axis extending along the height dimension of the keel punch; and a punch guide configured to closely receive the keel punch, the punch guide having a guide distal end distally disposed from a guide proximal end along a guide body, wherein the guide distal end is disposed at a guide posterior angle relative to a guide longitudinal axis extending along a height dimension of the punch guide, and wherein the guide distal end is disposed at a guide varus angle relative to a guide longitudinal axis extending along the height dimension of the punch guide.

An exemplary instrument assembly can further comprise a trial tibial baseplate, wherein the guide distal end further comprises spikes configured to extend through holes in the trial tibial baseplate.

An exemplary instrument assembly can further comprise a reamer extending through a through channel defined by an inner wall of the guide body of the punch guide to from the guide proximal end to the guide distal end.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A tibial component of an endoprosthetic knee implant configured to be implanted on a resected proximal end of a tibia, the tibial component comprising:

- a tibial base plate having an upper surface, a lower surface, an anterior side distally disposed from a posterior side, and a medial side distally disposed from a lateral side,
  - wherein a first line connecting the anterior side and the posterior side defines an anterior-posterior line,
  - wherein a second line connecting the medial side to the lateral side defines a medial-lateral line,
  - wherein a tibial baseplate plane is coplanar with the length and width of the baseplate, and
  - wherein the anterior-posterior line is disposed perpendicular to the medial-lateral line on the tibial baseplate plane; and
- a keel extending from the lower surface of the tibial baseplate to a distal end, wherein a keel longitudinal axis extends axially through the keel from the lower surface of the tibial baseplate to the distal end of the keel,
  - wherein the anterior-posterior line of the tibial baseplate is disposed at a posterior slope relative to a transverse plane intersecting the tibial component,
  - wherein the medial-lateral line of the tibial baseplate is disposed at a varus tilt relative to the transverse plane intersecting the tibial component,
  - wherein the tibial baseplate is disposed at a keel posterior angle relative to the keel longitudinal axis, the keel posterior angle being less than 90 degrees and greater than or equal to about 75 degrees,
  - wherein the tibial baseplate is disposed at a keel varus angle relative to the keel longitudinal axis, the keel varus angle being less than 90 degrees and greater than or equal to about 83 degrees, and
  - wherein the keel longitudinal axis is substantially aligned with the longitudinal axis of the tibia.

2. The tibial component of claim 1, wherein a distal stem extension is removably engaged to the keel.

3. The tibial component of claim 1, wherein the keel is a modular keel, and wherein the modular keel is removably engaged to the tibial baseplate.

4. The tibial component of claim 1, wherein the keel longitudinal axis is aligned with the longitudinal axis of the tibia in both the sagittal plane and the coronal plane when the tibial component is disposed in an installed configuration.

5. The tibial component of claim 1, wherein the posterior slope is greater than zero degrees and is less than or equal to about 15 degrees.

6. The tibial component of claim 5, wherein a distal stem extension is removably engaged to the keel.

7. The tibial component of claim 6, wherein the distal stem extension comprises grooves.

8. The tibial component of claim 5, wherein the keel is removably engaged to the tibial baseplate.

9. The tibial component of claim 1, wherein the varus tilt is greater than zero degrees and is greater than or equal to about 7 degrees.

10. The tibial component of claim 1, wherein the tibial baseplate plane is parallel to the anterior-posterior line and the medial-lateral line.

11. The tibial component of claim 1, wherein the keel is unitary with the tibial baseplate.

12. The tibial component of claim 1, wherein the keel further comprises one or more fins extending outwardly from the keel.

13. The tibial component of claim 1, wherein the tibial component comprises cobalt-chromium alloys, titanium, titanium alloys, zirconium, zirconium alloys, nickel, nickel alloys or a combination thereof.

14. The tibial component of claim 1, wherein the tibial component comprises a ceramic coating.

15. The tibial component of claim 1, wherein the distal end of the keel is rounded.

16. The tibial component of claim 1, wherein the distal end of the keel is straight, wedge shaped, wedge shaped with a rounded end, conical, conical with a rounded end, frustoconical, frustoconical with a rounded end, pyramidal, pyramidal with a rounded end, frustopyramidal, frustopyramidal with a rounded end, or a combination thereof.

17. The tibial component of claim 1, wherein the lower surface of the tibial baseplate is configured to engage the resected proximal end of the tibia.

18. The tibial component of claim 17, wherein the lower surface of the tibial baseplate is configured with projections to engage the resected proximal end of the tibia.

19. The tibial component of claim 18, wherein the projections comprise spikes.

20. The tibial component of claim 17, wherein the lower surface of the tibial baseplate is configured with a porous surface to engage the resected proximal end of the tibia.

* * * * *